(12) United States Patent
Jiao et al.

(10) Patent No.: US 9,780,315 B2
(45) Date of Patent: Oct. 3, 2017

(54) HETEROACENE COMPOUNDS FOR ORGANIC ELECTRONICS

(71) Applicant: BASF SE, Ludwigshafen (DE)

(72) Inventors: Chongjun Jiao, Singapore (SG); Iori Doi, Singapore (SG); Hans Jürg Kirner, Basel (CH); Mi Zhou, Singapore (SG); Thomas Weitz, Mannheim (DE); Ashok Kumar Mishra, Singapore (SG)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/649,039

(22) PCT Filed: Nov. 25, 2013

(86) PCT No.: PCT/IB2013/060391
§ 371 (c)(1),
(2) Date: Jun. 2, 2015

(87) PCT Pub. No.: WO2014/087300
PCT Pub. Date: Jun. 12, 2014

(65) Prior Publication Data
US 2015/0318496 A1 Nov. 5, 2015

(30) Foreign Application Priority Data
Dec. 3, 2012 (EP) .................... 12195227

(51) Int. Cl.
*H01L 51/00* (2006.01)
*H01L 51/05* (2006.01)
*C07D 495/22* (2006.01)

(52) U.S. Cl.
CPC ........ *H01L 51/0074* (2013.01); *C07D 495/22* (2013.01); *H01L 51/0545* (2013.01); *H01L 51/0558* (2013.01)

(58) Field of Classification Search
CPC ............................ C07D 495/22; H01L 51/00
See application file for complete search history.

(56) References Cited

U.S. PATENT DOCUMENTS

| 2008/0142792 A1 | 6/2008 | Park et al. |
| 2011/0210319 A1 | 9/2011 | Nakano et al. |

FOREIGN PATENT DOCUMENTS

| EP | 1932847 A1 | 6/2008 |
| JP | 2009-70986 | 4/2009 |
| JP | 2010177643 A | 8/2010 |
| JP | 2011-86836 | 4/2011 |
| JP | 2015-502937 | 1/2015 |
| WO | WO-2011067192 A2 | 6/2011 |
| WO | WO-2013/039842 A1 | 3/2013 |

OTHER PUBLICATIONS

Rieger et al., 2010, caplus an 2010:873320.*
Murthy et al., 1961, caplus an 1961:144083.*
Facchetti et al., caplus an 2013:836280 (2013).*
International Search Report for PCT/IB2013/060391 mailed May 8, 2014.
Office Action dated Oct. 18, 2016 for Korean Application No. 10-2015-7017460 with English Translation.
Rieger, Ralph, et al. Macromolecules 2010, 43(15), 6264 to 6267.
Rieger, Ralph, et al. Macromolecules 2010, 43(15), 6264 to 6267. Supporting Information.
Extended European Search Report issued Jun. 28, 2016 in PCT/IB2013/060391.
Japanese Office Action dated Jun. 30, 2016 in Japanese Application No. 2015-546122 with English Translation.

* cited by examiner

*Primary Examiner* — Sun Jae Yoo
(74) *Attorney, Agent, or Firm* — Oblon, McClelland, Maier & Neustadt, L.L.P.

(57) ABSTRACT

The present invention provides compounds of formula (1) wherein o is 1, 2 or 3, p is 0, 1 or 2, n is 0, 1 or 2, m is 0, 1 or 2, and A is a mono- or polycyclic ring system, which may contain at least one heteroatom, and an electronic device comprising the compounds as semiconducting material.

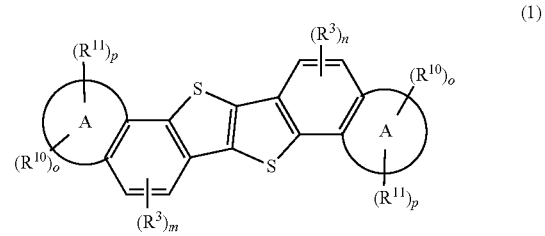

11 Claims, 3 Drawing Sheets

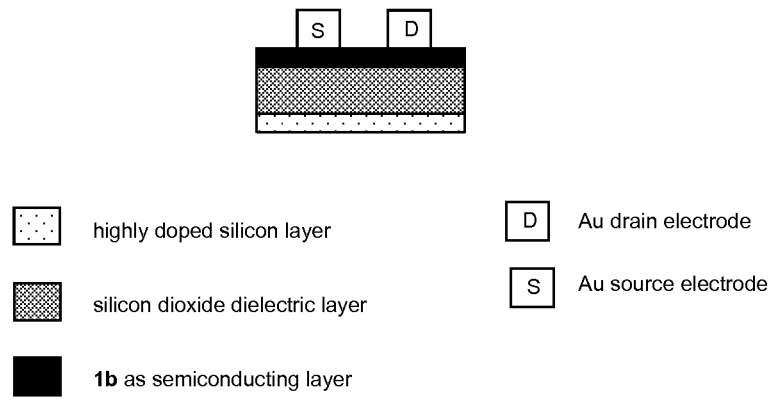
Figure 1: bottom gate top contact organic field effect transistor of example 3.
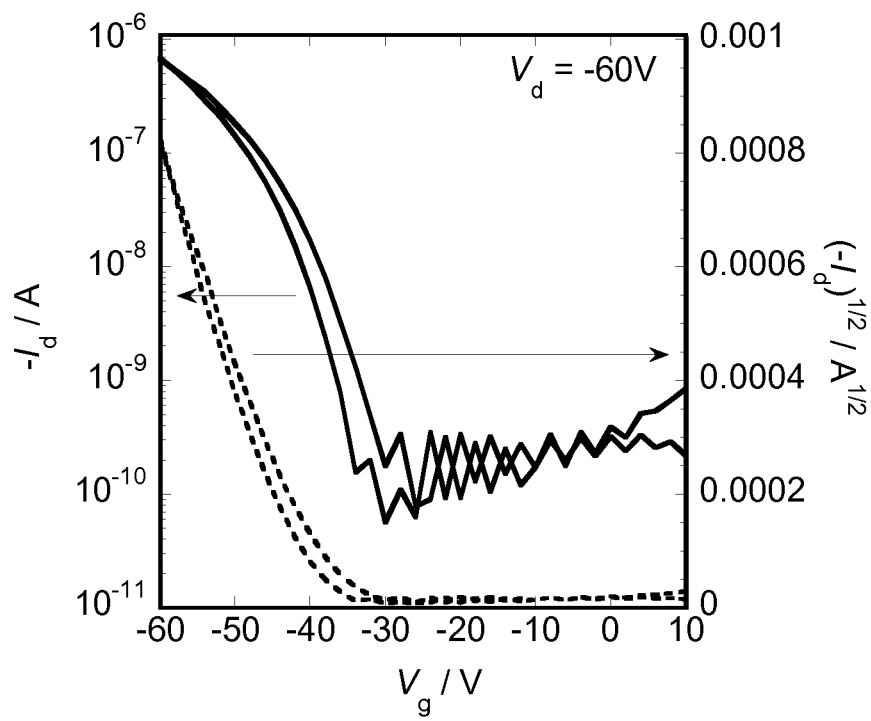
Figure 2: transfer curves of compound 1b.

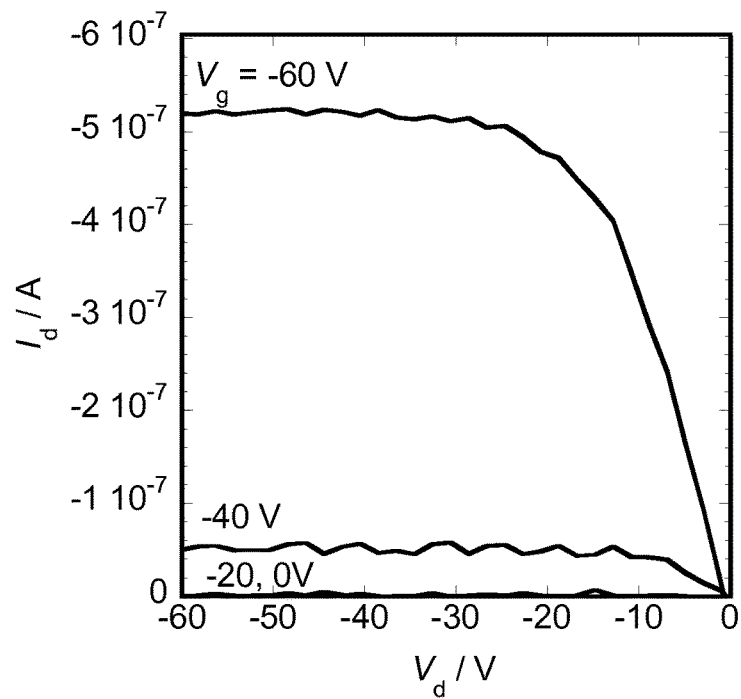
Figure 3: output curves of compound 1b.
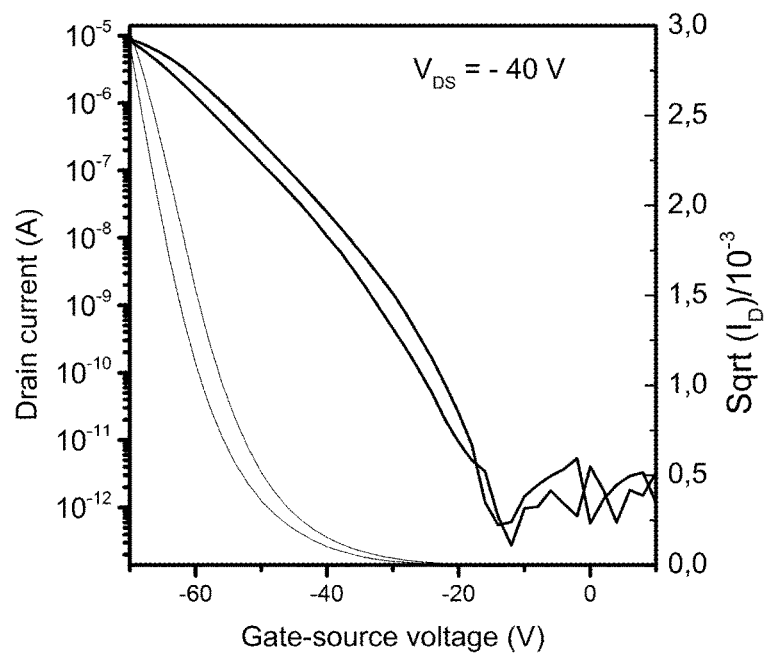
Figure 4: transfer curves of compound 1a.

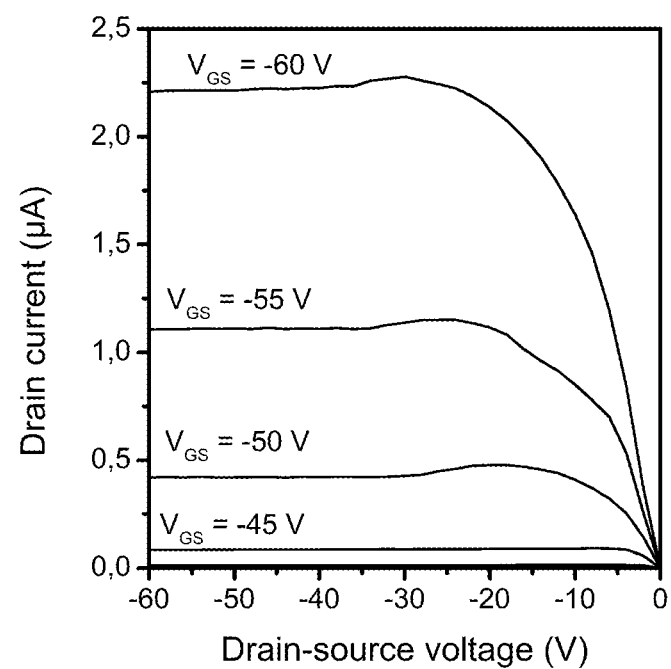
Figure 5: output curves of compound 1a.

HETEROACENE COMPOUNDS FOR ORGANIC ELECTRONICS

CROSS-REFERENCE TO RELATED APPLICATIONS

This application is a national stage application (under 35 U.S.C. §371) of PCT/IB2013/060391, filed Nov. 25. 2013, which claims benefit of European Application No. 12195227.9, filed Dec. 3, 2012, both of which are incorporated herein by reference in their entirety.

Organic semiconducting materials can be used in electronic devices such as organic photovoltaic devices (OPVs), organic field-effect transistors (OFETs), organic light emitting diodes (OLEDs), and organic electrochromic devices (ECDs).

For efficient and long lasting performance, it is desirable that the organic semiconducting material-based devices show high charge carrier mobility as well as high stability, in particular towards oxidation by air.

Furthermore, it is desirable that the organic semiconducting materials are compatible with liquid processing techniques such as spin coating as liquid processing techniques are convenient from the point of processability, and thus allow the production of low cost organic semiconducting material-based electronic devices. In addition, liquid processing techniques are also compatible with plastic substrates, and thus allow the production of light weight and mechanically flexible organic semiconducting material-based electronic devices.

The organic semiconducting materials can be either p-type or n-type organic semiconducting materials. It is desirable that both types of organic semiconducting materials are available for the production of electronic devices.

The use of heteroacene compounds containing thieno units as p-type semiconducting materials in electronic devices is known in the art.

WO 2011/067192 describes copolymers of the general formula

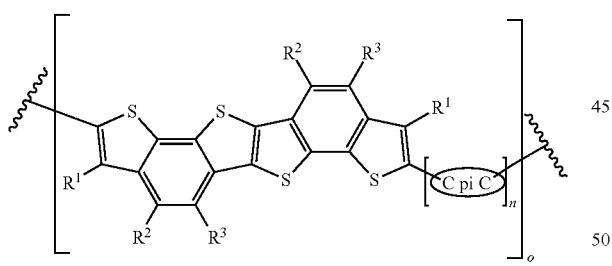

and in particular the copolymer of formula

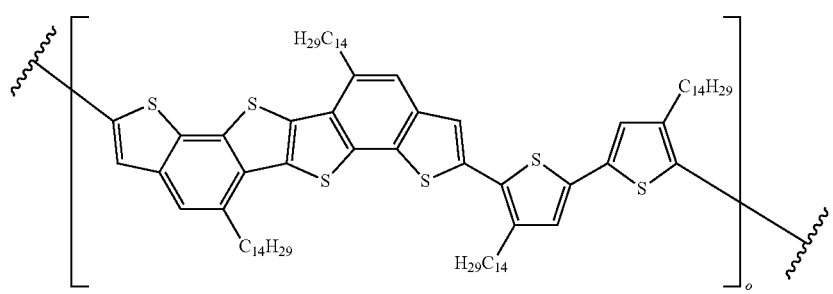

An organic field effect transistor (OFET) containing this particular copolymer as semiconducting material shows a charge carrier mobility of 1.29 ($\pm$0.28)*$10^{-3}$ $cm^2/V$ s and an on-off ratio of 3.8 ($\pm$0.2)*$10^3$.

Wang, J.; Y; Zhou, Y.; Yan, J.; Ding, L.; Ma, Y.; Cao, Y.; Wang, J.; Pei, J. Chem. Mater. 2009, 21, 2595 to 2597 describes the following compounds

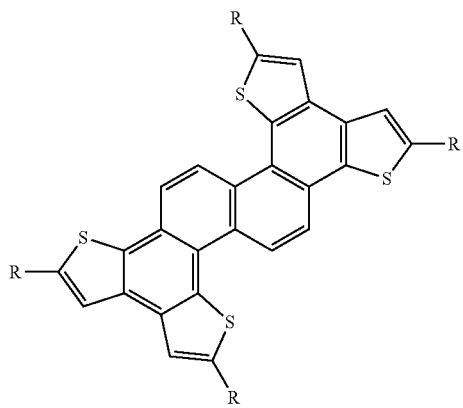

R = n-$C_3H_7$ or n-$C_6H_{13}$

An organic field effect transistor (OFET) containing one of these compounds as p-type semiconducting material shows a charge carrier mobility up to 0.4 $cm^2/V$ s.

US 2008/142792 describes compounds of general formula

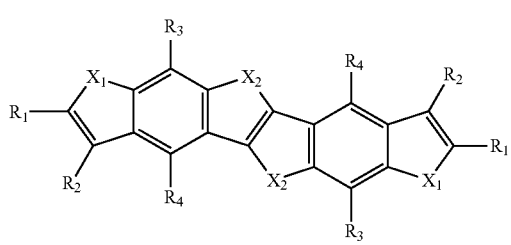

and

-continued

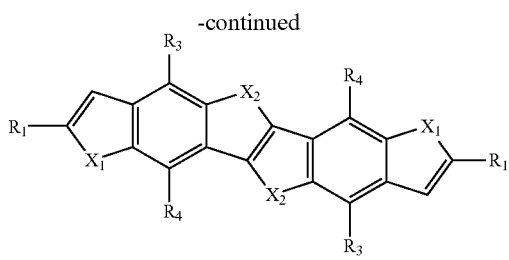

An organic field effect transistor (OFET) containing the following compound

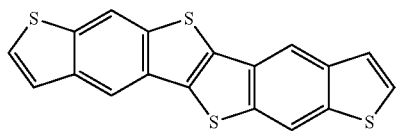 [SMILES: c1cc2cc3c(cc2s1)sc1c2cc4ccsc4cc2sc31]

shows a charge carrier mobility of 0.08 cm²/V s.

Yamamoto, T.; Takimiya, K. *J. Am. Chem. Soc.* 2007, 129, 2224 to 2225 describe

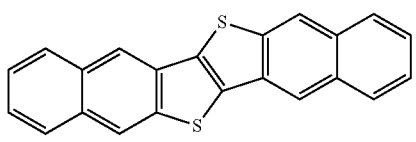

An organic field effect transistor (OFET) containing DNTT shows a charge carrier mobility of higher than 2.0 cm²/V s and an on-off ratio of >10⁷.

Nakayama, K.; Hirose, Y.; Soeda, J.; Yoshizumi, M.; Uemura, T.; Uno, M.; Li, W.; Kang, M. J.; Yamagishi, M.; Okada, Y.; Miyazaki, E.; Y. Nakazawa, Y.; Nakao, A.; Takimiya, K.; Takeya, J. *Adv. Mater.* 2011, 23, 1626 to 1629 describes the preparation of organic field effect transistor (OFET) containing $C_{10}$-DNTT having the following formula

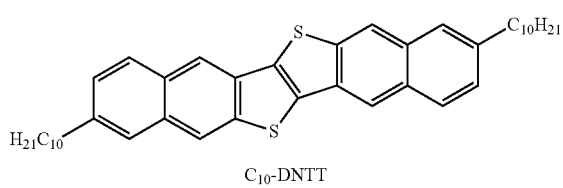

The deposition of $C_{10}$-DNTT was performed from an approximately 100° C. hot solution of $C_{10}$-DNTT in 1,2-dichlorobenzene. The organic field effect transistors (OFET) containing $C_{10}$-DNTT show charge carrier mobilities exceeding 10.0 cm²/V s.

Niimi, K.; Shinamura, S.; Osaka, I.; Miyazaki, E.; Takimiya, K. *J. Am. Chem Soc.* 2011, 133, 8732 to 8739 describes the following compound

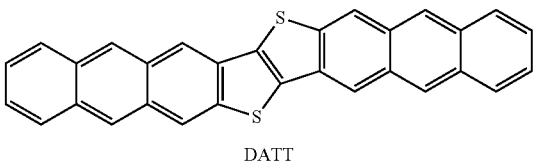

A charge carrier mobility as high as 3.0 cm²/V s was achieved with vapor-processed DATT-based devices.

US 2011/0210319 describes organic field effect transistor (OFET) containing the following π-extended S-containing heteroarene compounds

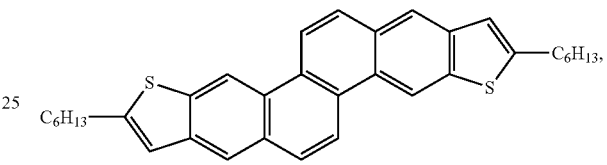

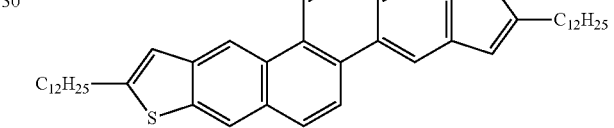

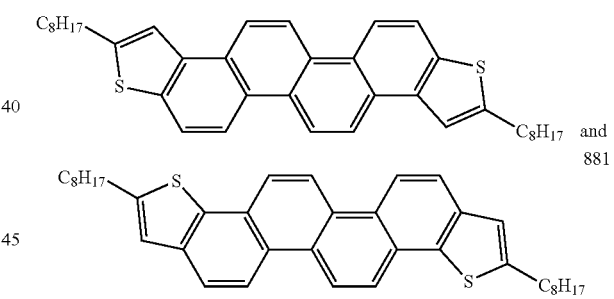

These OFETs show the following charge carrier mobilities: 1.2 (compound 167), 1.8 (compound 250), 2.0 (compound 638), 1.7 (compound 881) cm²/V s, and the following on-off ratios: 2*10⁶ (compound 167), 3*10⁶ (compound 250), 4*10⁵ (compound 638) and 3*10⁶ (compound 881).

WO 2013/039842 describes compounds of the following formula

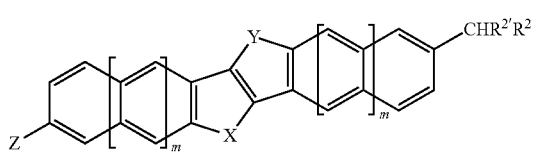

It was the object of the present invention to provide improved organic, preferably p-type, semiconducting materials.

This object is solved by the compounds of embodiment 1, the electronic device of embodiment 13 and the use of embodiment 15.

The organic semiconducting materials of the present invention are compounds of formula

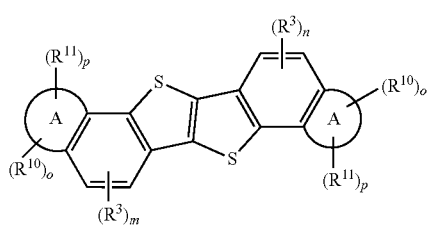

(1)

wherein
o is 1, 2 or 3,
p is 0, 1 or 2,
n is 0, 1 or 2,
m is 0, 1 or 2,
A is a mono- or polycyclic ring system, which may contain at least one heteroatom,
$R^{10}$ is at each occurrence selected from the group consisting of halogen, —CN, —NO$_2$, $C_{1-30}$-alkyl, $C_{2-30}$-alkenyl, $C_{2-30}$-alkynyl, $C_{4-8}$-cycloalkyl, $C_{6-14}$-aryl, and a 5 to 14 membered heterocyclic ring system, wherein
at least one CH$_2$-group of $C_{1-30}$-alkyl, $C_{2-30}$-alkenyl and $C_{2-30}$-alkynyl, but not adjacent CH$_2$-groups, may be replaced with —O— or —S—,
$C_{1-30}$-alkyl, $C_{2-30}$-alkenyl and $C_{2-30}$-alkynyl may be optionally substituted with 1 to 10 $R^{100}$ residues at each occurrence selected from the group consisting of halogen, —CN, —NO$_2$, —OH, —NH$_2$, —NH($R^a$), —N($R^a$)$_2$, —NH—C(O)—($R^a$), —N($R^a$)—C(O)—($R^a$), —N[C(O)—($R^a$)]$_2$, —C(O)—$R^a$, —C(O)—O$R^a$, —C(O)NH$_2$, —CO(O)NH—$R^a$, —C(O)N($R^a$)$_2$, —O—$R^a$, —O—C(O)—$R^a$, $C_{4-8}$-cycloalkyl, $C_{6-14}$-aryl, and a 5 to 14 membered heterocyclic ring system, and
wherein
$R^a$ is at each occurrence selected from the group consisting of $C_{1-20}$-alkyl, $C_{2-20}$-alkenyl, $C_{2-20}$-alkynyl, $C_{4-8}$-cycloalkyl, $C_{6-14}$-aryl, and a 5 to 14 membered heterocyclic ring system, wherein
$C_{1-20}$-alkyl, $C_{2-20}$-alkenyl and $C_{2-20}$-alkynyl may be substituted with 1 to 5 residues at each occurrence selected from the group consisting of halogen, CN, —NO$_2$, —OH, —NH$_2$, $C_{4-8}$-cycloalkyl, $C_{6-14}$-aryl, and a 5 to 14 membered heterocyclic ring system, and
$C_{4-8}$-cycloalkyl, $C_{6-14}$-aryl, and a 5 to 14 membered heterocyclic ring system may be substituted with 1 to 5 residues at each occurrence selected from the group consisting of halogen, CN, —NO$_2$, —OH, —NH$_2$, $C_{1-10}$-alkyl, $C_{2-10}$-alkenyl and $C_{2-10}$-alkynyl, and
$R^3$ and $R^{11}$ are independently from each other at each occurrence selected from the group consisting of halogen, —CN, —NO$_2$, $C_{1-30}$-alkyl, $C_{2-30}$-alkenyl, $C_{2-30}$-alkynyl, $C_{4-8}$-cycloalkyl, $C_{6-14}$-aryl, and a 5 to 14 membered heterocyclic ring system, wherein
at least one CH$_2$-group of $C_{1-30}$-alkyl, $C_{2-30}$-alkenyl and $C_{2-30}$-alkynyl, but not adjacent CH$_2$-groups, may be replaced with —O— or —S—, and $C_{1-30}$-alkyl, $C_{2-30}$-alkenyl and $C_{2-30}$-alkynyl may be optionally substituted with 1 to 10 $R^{101}$ residues independently selected from the group consisting of halogen, —CN, —NO$_2$, —OH, —NH$_2$, —NH($R^b$), —N($R^b$)$_2$, —NH—C(O)—($R^b$), —N($R^b$)—C(O)—($R^b$), —N[C(O)—($R^b$)]$_2$, —C(O)—$R^b$, —C(O)—O$R^b$, —C(O)NH$_2$, —CO(O)NH—$R^b$, —C(O)N($R^b$)$_2$, —O—$R^b$, —O—C(O)—$R^b$, $C_{4-8}$-cycloalkyl, $C_{6-14}$-aryl, and a 5 to 14 membered heterocyclic ring system, and wherein
wherein
$R^b$ is at each occurrence selected from the group consisting of $C_{1-20}$-alkyl, $C_{2-20}$-alkenyl, $C_{2-20}$-alkynyl, $C_{4-8}$-cycloalkyl, $C_{6-14}$-aryl, and a 5 to 14 membered heterocyclic ring system, wherein
$C_{1-20}$-alkyl, $C_{2-20}$-alkenyl or $C_{2-20}$-alkynyl may be substituted with 1 to 5 residues at each occurrence selected from the group consisting of halogen, CN, —NO$_2$, —OH, —NH$_2$, $C_{4-8}$-cycloalkyl, $C_{6-14}$-aryl, and a 5 to 14 membered heterocyclic ring system, and
$C_{4-8}$-cycloalkyl, $C_{6-14}$-aryl, and a 5 to 14 membered heterocyclic ring system may be substituted with 1 to 5 residues independently selected from the group consisting of halogen, CN, —NO$_2$, —OH, —NH$_2$, $C_{1-10}$-alkyl, $C_{2-10}$-alkenyl, and $C_{2-10}$-alkynyl.
Examples of monocyclic ring systems A are

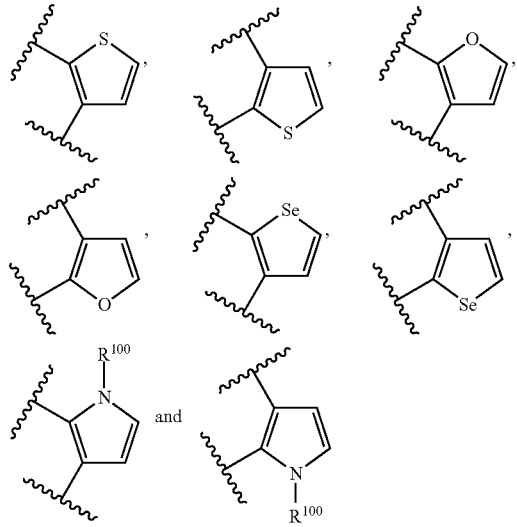

wherein $R^{100}$ is H or $C_{1-10}$-alkyl.
Examples of polycyclic ring systems A are

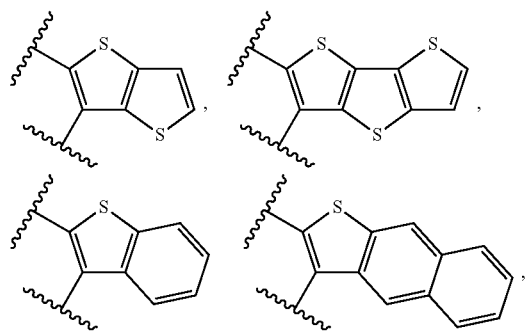

-continued

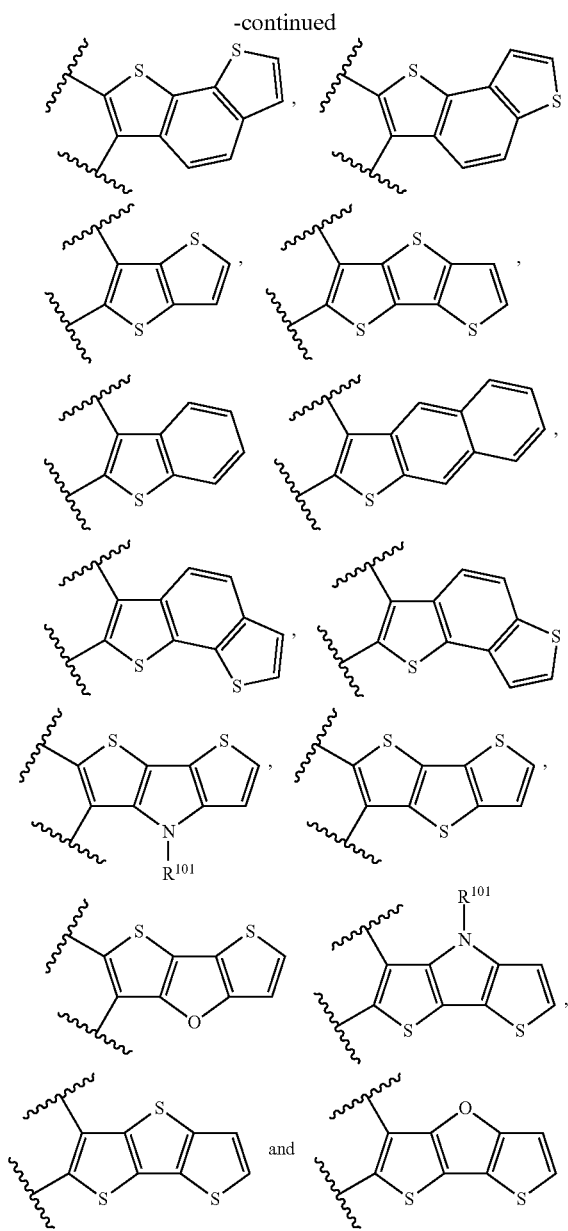

wherein R¹⁰¹ is H or $C_{1-10}$-alkyl.

$C_{1-10}$-alkyl, $C_{1-20}$-alkyl and $C_{1-30}$-alkyl can be branched or unbranched. Examples of $C_{1-10}$-alkyl are methyl, ethyl, n-propyl, isopropyl, n-butyl, sec-butyl, isobutyl, tert-butyl, n-pentyl, neopentyl, isopentyl, n-(1-ethyl)propyl, n-hexyl, n-heptyl, n-octyl, n-(2-ethyl)hexyl, n-nonyl and n-decyl. Examples of $C_{1-20}$-alkyl are $C_{1-10}$-alkyl and n-undecyl, n-dodecyl, n-undecyl, n-dodecyl, n-tridecyl, n-tetradecyl, n-pentadecyl, n-hexadecyl, n-heptadecyl, n-octadecyl, n-nonadecyl and n-icosyl ($C_{20}$). Examples of $C_{1-30}$-alkyl are $C_{1-20}$-alkyl and n-docosyl ($C_{22}$), n-tetracosyl ($C_{24}$), n-hexacosyl ($C_{26}$), n-octacosyl ($C_{28}$) and n-triacontyl ($C_{30}$). Examples of $C_{8-20}$-alkyl are n-octyl, n-(2-ethyl)-hexyl, n-nonyl, n-decyl, n-undecyl, n-dodecyl, n-undecyl, n-dodecyl, n-tridecyl, n-tetradecyl, n-pentadecyl, n-hexadecyl, n-heptadecyl, n-octadecyl, n-nonadecyl and n-icosyl ($C_{20}$)

$C_{2-10}$-alkenyl, $C_{2-20}$-alkenyl and $C_{2-30}$-alkenyl can be branched or unbranched. Examples of $C_{1-20}$-alkenyl are vinyl, propenyl, cis-2-butenyl, trans-2-butenyl, 3-butenyl, cis-2-pentenyl, trans-2-pentenyl, cis-3-pentenyl, trans-3-pentenyl, 4-pentenyl, 2-methyl-3-butenyl, hexenyl, heptenyl, octenyl, nonenyl and docenyl. Examples of $C_{2-20}$-alkenyl are $C_{2-10}$-alkenyl and linoleyl ($C_{18}$), linolenyl ($C_{18}$), oleyl ($C_{18}$), and arachidonyl ($C_{20}$). Examples of $C_{2-30}$-alkenyl are $C_{2-20}$-alkenyl and erucyl ($C_{22}$).

$C_{2-10}$-alkynyl, $C_{2-20}$-alkynyl and $C_{2-30}$-alkenyl can be branched or unbranched. Examples of $C_{2-10}$-alkynyl are ethynyl, 2-propynyl, 2-butynyl, 3-butynyl, pentynyl, hexynyl, heptynyl, octynyl, nonynyl and decynyl. Examples of $C_{2-20}$-alkynyl and $C_{2-30}$-alkenyl are undecynyl, dodecynyl, undecynyl, dodecynyl, tridecynyl, tetradecynyl, pentadecynyl, hexadecynyl, heptadecynyl, octadecynyl, nonadecynyl and icosynyl ($C_{20}$).

Examples of $C_{4-8}$-cycloalkyl are cyclobutyl, cyclopentyl, cyclohexyl, cycloheptyl and cyclooctyl.

Examples of $C_{6-14}$-aryl are phenyl and naphthyl.

The 5 to 14 membered heterocyclic ring systems can be monocyclic or polycyclic.

Examples of 5 to 14 membered heterocyclic ring systems are pyrrolidinyl, 1-pyrrolinyl, 2-pyrrolinyl, 3-pyrrolinyl, tetrahydrofuryl, 2,3-dihydrofuryl, tetrahydrothiophenyl, 2,3-dihydrothiophenyl, imidazolidinyl, imidazolinyl, pyrazolidinyl, pyrazolinyl, oxazolidinyl, oxazolinyl, isoxazolidinyl, isoxazolinyl, thiazolidinyl, thiazolinyl, isothiazolidinyl, isothiazolinyl, 1,2,3-triazolyl, 1,2,4-triazolyl, 1,4,2-dithiazolyl, piperidyl, piperidino, tetrahydropyranyl, pyranyl, thianyl, thiopyranyl, piperazinyl, morpholinyl and morpholino, thiazinyl, azepinyl, azepinyl, oxepanyl, thiepanyl, thiapanyl, thiepinyl, 1,2-diazepinyl, 1,3-thiazepinyl, decahydronaphthyl, pyrrolyl, furyl, thiophenyl, imidazolyl, pyrazolyl, oxazolyl, isoxazolyl, thiazolyl, isothiazolyl, 1,2,3-triazolyl, 1,2,4-triazolyl, oxadiazolyl, tetrazolyl, pyridyl, pyrazinyl, pyrimidinyl and pyridazinyl, 1,2,3-triazinyl, 1,2,4-triazinyl, 1,3,5-triazinyl, azepinyl and 1,2-diazepinyl.

Examples of halogen are F, Cl, Br and I.

Preferably, o is 1 or 2. More preferably, o is 1.

Preferably, p, n and m are 0 or 1. More preferably, p, n and m are 0.

Preferably, A is a mono- or dicyclic ring system A, which contains at least one heteroatom.

More preferably, A is a mono- or dicyclic ring system A, which contains at least one S atom.

Most preferably, A is a monocyclic ring system A, which contains at least one S atom.

In particular A is

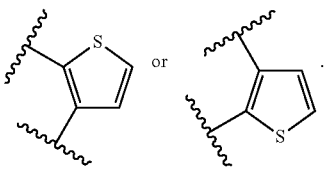

Preferably, R¹⁰ is at each occurrence selected from the group consisting of $C_{1-30}$-alkyl, $C_{4-8}$-cycloalkyl, $C_{6-14}$-aryl, and a 5 to 14 membered heterocyclic ring system, wherein at least one $CH_2$-group of $C_{1-30}$-alkyl, but not adjacent $CH_2$-groups, may be replaced with —O— or —S—, $C_{1-30}$-alkyl may be optionally substituted with 1 to 10 R¹⁰⁰ residues at each occurrence selected from the group consisting of halogen, —CN, —NO₂, —OH, —NH₂, —NH(Rᵃ), —N(Rᵃ)₂, —NH—C(O)—(Rᵃ), —N(Rᵃ)—C(O)—(Rᵃ), —N[C(O)—(Rᵃ)]₂, —C(O)—Rᵃ, —C(O)—ORᵃ, —C(O)NH₂, —CO(O)NH—Rᵃ, —C(O)N($R^a$)$_2$, —O—$R^a$, —O—C(O)—$R^a$, $C_{4-8}$-cycloalkyl, $C_{6-14}$-aryl, and a 5 to 14 membered heterocyclic ring system, and
wherein
$R^a$ is at each occurrence selected from the group consisting of $C_{1-20}$-alkyl, $C_{2-20}$-alkenyl, $C_{2-20}$-alkynyl, $C_{4-8}$-cycloalkyl, $C_{6-14}$-aryl, and a 5 to 14 membered heterocyclic ring system, wherein
$C_{1-20}$-alkyl, $C_{2-20}$-alkenyl and $C_{2-20}$-alkynyl may be substituted with 1 to 5 residues at each occurrence selected from the group consisting of halogen, CN, —NO$_2$, —OH, —NH$_2$, $C_{4-8}$-cycloalkyl, $C_{6-14}$-aryl, and a 5 to 14 membered heterocyclic ring system, and
$C_{4-8}$-cycloalkyl, $C_{6-14}$-aryl, and a 5 to 14 membered heterocyclic ring system may be substituted with 1 to 5 residues at each occurrence selected from the group consisting of halogen, CN, —NO$_2$, —OH, —NH$_2$, $C_{1-10}$-alkyl, $C_{2-10}$-alkenyl and $C_{2-10}$-alkynyl.

More preferably, $R^{10}$ is at each occurrence $C_{1-30}$-alkyl, wherein
at least one CH$_2$-group of $C_{1-30}$-alkyl, but not adjacent CH$_2$-groups, may be replaced with —O— or —S—,
$C_{1-30}$-alkyl may be optionally substituted with 1 to 10 $R^{100}$ residues at each occurrence selected from the group consisting of halogen, —CN, —NO$_2$, —OH, —NH$_2$, —NH($R^a$), —N($R^a$)$_2$, —NH—C(O)—($R^a$), —N($R^a$)—C(O)—($R^a$), —N[C(O)—($R^a$)]$_2$, —C(O)—$R^a$, —C(O)—O$R^a$, —C(O)NH$_2$, —CO(O)NH—$R^a$, —C(O)N($R^a$)$_2$, —O—$R^a$, —O—C(O)—$R^a$, $C_{4-8}$-cycloalkyl, $C_{6-14}$-aryl, and a 5 to 14 membered heterocyclic ring system, and
wherein
$R^a$ is at each occurrence selected from the group consisting of $C_{1-20}$-alkyl, $C_{2-20}$-alkenyl, $C_{2-20}$-alkynyl, $C_{4-8}$-cycloalkyl, $C_{6-14}$-aryl, and a 5 to 14 membered heterocyclic ring system, wherein
$C_{1-20}$-alkyl, $C_{2-20}$-alkenyl and $C_{2-20}$-alkynyl may be substituted with 1 to 5 residues at each occurrence selected from the group consisting of halogen, CN, —NO$_2$, —OH, —NH$_2$, $C_{4-8}$-cycloalkyl, $C_{6-14}$-aryl, and a 5 to 14 membered heterocyclic ring system.

Even more preferably, $R^{10}$ is at each occurrence $C_{1-30}$-alkyl.

Most preferably, $R^{10}$ is at each occurrence $C_{8-20}$-alkyl.

In particular, $R^{10}$ is at each occurrence $C_{14}H_{29}$.

Preferably, $R^3$ and $R^{11}$ are independently from each other at each occurrence selected from the group consisting of halogen, —CN, $C_{1-30}$-alkyl, $C_{4-8}$-cycloalkyl, $C_{6-14}$-aryl, and a 5 to 14 membered heterocyclic ring system, wherein
at least one CH$_2$-group of $C_{1-30}$-alkyl, but not adjacent CH$_2$-groups, may be replaced with —O— or —S—, and
$C_{1-30}$-alkyl may be optionally substituted with 1 to 10 $R^{101}$ residues independently selected from the group consisting of halogen, —CN, —NO$_2$, —OH, —NH$_2$, —NH($R^b$), —N($R^b$)$_2$, —NH—C(O)—($R^b$), —N($R^b$)—C(O)—($R^b$), —N[C(O)—($R^b$)]$_2$, —C(O)—$R^b$, —C(O)—O$R^b$, —C(O)NH$_2$, —CO(O)NH—$R^b$, —C(O)N($R^b$)$_2$, —O—$R^b$, —O—C(O)—$R^b$, $C_{4-8}$-cycloalkyl, $C_{6-14}$-aryl, and a 5 to 14 membered heterocyclic ring system, and wherein
wherein
$R^b$ is at each occurrence selected from the group consisting of $C_{1-20}$-alkyl, $C_{2-20}$-alkenyl, $C_{2-20}$-alkynyl, $C_{4-8}$-cycloalkyl, $C_{6-14}$-aryl, and a 5 to 14 membered heterocyclic ring system, wherein
$C_{1-20}$-alkyl, $C_{2-20}$-alkenyl or $C_{2-20}$-alkynyl may be substituted with 1 to 5 residues at each occurrence selected from the group consisting of halogen, CN, —NO$_2$, —OH, —NH$_2$, $C_{4-8}$-cycloalkyl, $C_{6-14}$-aryl, and a 5 to 14 membered heterocyclic ring system, and
$C_{4-8}$-cycloalkyl, $C_{6-14}$-aryl, and a 5 to 14 membered heterocyclic ring system may be substituted with 1 to 5 residues independently selected from the group consisting of halogen, CN, —NO$_2$, —OH, —NH$_2$, $C_{1-10}$-alkyl, $C_{2-10}$-alkenyl, and $C_{2-10}$-alkynyl.

More preferably, $R^3$ and $R^{11}$ are independently from each other at each occurrence selected from the group consisting of $C_{1-30}$-alkyl, $C_{6-14}$-aryl, and a 5 to 14 membered heterocyclic ring system, wherein
at least one CH$_2$-group of $C_{1-30}$-alkyl, but not adjacent CH$_2$-groups, may be replaced with —O— or —S—, and
$C_{1-30}$-alkyl may be optionally substituted with 1 to 10 $R^{101}$ residues independently selected from the group consisting of halogen, —CN, —NO$_2$, —OH, —NH$_2$, —NH($R^b$), —N($R^b$)$_2$, —NH—C(O)—($R^b$), —N($R^b$)—C(O)—($R^b$), —N[C(O)—($R^b$)]$_2$, —C(O)—$R^b$, —C(O)—O$R^b$, —C(O)NH$_2$, —CO(O)NH—$R^b$, —C(O)N($R^b$)$_2$, —O—$R^b$, —O—C(O)—$R^b$, $C_{4-8}$-cycloalkyl, $C_{6-14}$-aryl, and a 5 to 14 membered heterocyclic ring system, and wherein
wherein
$R^b$ is at each occurrence selected from the group consisting of $C_{1-20}$-alkyl, $C_{2-20}$-alkenyl, $C_{2-20}$-alkynyl, $C_{4-8}$-cycloalkyl, $C_{6-14}$-aryl, and a 5 to 14 membered heterocyclic ring system, wherein
$C_{1-20}$-alkyl, $C_{2-20}$-alkenyl or $C_{2-20}$-alkynyl may be substituted with 1 to 5 residues at each occurrence selected from the group consisting of halogen, CN, —NO$_2$, —OH, —NH$_2$, $C_{4-8}$-cycloalkyl, $C_{6-14}$-aryl, and a 5 to 14 membered heterocyclic ring system, and
$C_{6-14}$-aryl, and a 5 to 14 membered heterocyclic ring system may be substituted with 1 to 5 residues independently selected from the group consisting of halogen, CN, —NO$_2$, —OH, —NH$_2$, $C_{1-10}$-alkyl, $C_{2-10}$-alkenyl, and $C_{2-10}$-alkynyl.

Even more preferably, $R^3$ and $R^{11}$ are independently from each other at each occurrence $C_{1-30}$-alkyl.

Preferred are compounds of formula

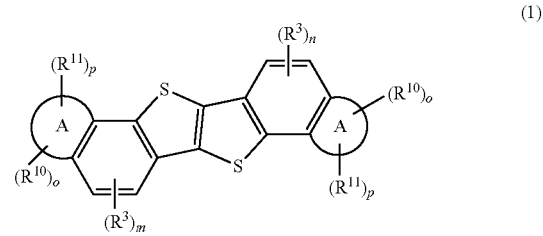

wherein
o is 1, 2 or 3,
p is 0, 1 or 2,
n is 0, 1 or 2,
m is 0, 1 or 2,

A is a mono- or dicyclic ring system, which contains at least one heteroatom, $R^{10}$ is at each occurrence $C_{1-30}$-alkyl, wherein
at least one $CH_2$-group of $C_{1-30}$-alkyl, but not adjacent $CH_2$-groups, may be replaced with —O— or —S—,
$C_{1-30}$-alkyl may be optionally substituted with 1 to 10 $R^{100}$ residues at each occurrence selected from the group consisting of halogen, —CN, —NO$_2$, —OH, —NH$_2$, —NH($R^a$), —N($R^a$)$_2$, —NH—C(O)—($R^a$), —N($R^a$)—C(O)—($R^a$), —N[C(O)—($R^a$)]$_2$, —C(O)—$R^a$, —C(O)—O$R^a$, —C(O)NH$_2$, —CO(O)NH—$R^a$, —C(O)N($R^a$)$_2$, —O—$R^a$, —O—C(O)—$R^a$, $C_{4-8}$-cycloalkyl, $C_{6-14}$-aryl, and a 5 to 14 membered heterocyclic ring system, and wherein
$R^a$ is at each occurrence selected from the group consisting of $C_{1-20}$-alkyl, $C_{2-20}$-alkenyl, $C_{2-20}$-alkynyl, $C_{4-8}$-cycloalkyl, $C_{6-14}$-aryl, and a 5 to 14 membered heterocyclic ring system, wherein
$C_{1-20}$-alkyl, $C_{2-20}$-alkenyl and $C_{2-20}$-alkynyl may be substituted with 1 to 5 residues at each occurrence selected from the group consisting of halogen, CN, —NO$_2$, —OH, —NH$_2$, $C_{4-8}$-cycloalkyl, $C_{6-14}$-aryl, and a 5 to 14 membered heterocyclic ring system, and $R^3$ and $R^{11}$ are independently from each other at each occurrence selected from the group consisting of halogen, —CN, $C_{1-30}$-alkyl, $C_{4-8}$-cycloalkyl, $C_{6-14}$-aryl, and a 5 to 14 membered heterocyclic ring system, wherein
at least one $CH_2$-group of $C_{1-30}$-alkyl, but not adjacent $CH_2$-groups, may be replaced with —O— or —S—, and
$C_{1-30}$-alkyl may be optionally substituted with 1 to 10 $R^{101}$ residues independently selected from the group consisting of halogen, —CN, —NO$_2$, —OH, —NH$_2$, —NH($R^b$), —N($R^b$)$_2$, —NH—C(O)—($R^b$), —N($R^b$)—C(O)—($R^b$), —N[C(O)—($R^b$)]$_2$, —C(O)—$R^b$, —C(O)—O$R^b$, —C(O)NH$_2$, —CO(O)NH—$R^b$, —C(O)N($R^b$)$_2$, —O—$R^b$, —O—C(O)—$R^b$, $C_{4-8}$-cycloalkyl, $C_{6-14}$-aryl, and a 5 to 14 membered heterocyclic ring system, and wherein wherein
$R^b$ is at each occurrence selected from the group consisting of $C_{1-20}$-alkyl, $C_{2-20}$-alkenyl, $C_{2-20}$-alkynyl, $C_{4-8}$-cycloalkyl, $C_{6-14}$-aryl, and a 5 to 14 membered heterocyclic ring system, wherein
$C_{1-20}$-alkyl, $C_{2-20}$-alkenyl or $C_{2-20}$-alkynyl may be substituted with 1 to 5 residues at each occurrence selected from the group consisting of halogen, CN, —NO$_2$, —OH, —NH$_2$, $C_{4-8}$-cycloalkyl, $C_{6-14}$-aryl, and a 5 to 14 membered heterocyclic ring system, and
$C_{4-8}$-cycloalkyl, $C_{6-14}$-aryl, and a 5 to 14 membered heterocyclic ring system may be substituted with 1 to 5 residues independently selected from the group consisting of halogen, CN, —NO$_2$, —OH, —NH$_2$, $C_{1-10}$-alkyl, $C_{2-10}$-alkenyl, and $C_{2-10}$-alkynyl.

More preferred are compounds of formula

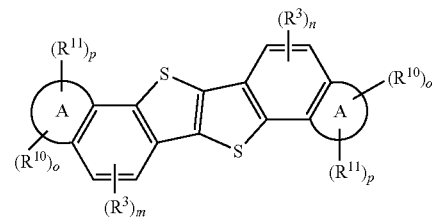

(1)

wherein
o is 1 or 2,
p is 0 or 1,
n is 0 or 1,
m is 0 or 1,
A is a mono- or dicyclic ring system A, which contains at least S atom,
$R^{10}$ is at each occurrence $C_{1-30}$-alkyl, and
$R^3$ and $R^{11}$ are independently from each other at each occurrence selected from the group consisting of $C_{1-30}$-alkyl, $C_{6-14}$-aryl, and a 5 to 14 membered heterocyclic ring system, wherein
at least one $CH_2$-group of $C_{1-30}$-alkyl, but not adjacent $CH_2$-groups, may be replaced with —O— or —S—, and
$C_{1-30}$-alkyl may be optionally substituted with 1 to 10 $R^{101}$ residues independently selected from the group consisting of halogen, —CN, —NO$_2$, —OH, —NH$_2$, —NH($R^b$), —N($R^b$)$_2$, —NH—C(O)—($R^b$), —N($R^b$)—C(O)—($R^b$), —N[C(O)—($R^b$)]$_2$, —C(O)—$R^b$, —C(O)—O$R^b$, —C(O)NH$_2$, —CO(O)NH—$R^b$, —C(O)N($R^b$)$_2$, —O—$R^b$, —O—C(O)—$R^b$, $C_{4-8}$-cycloalkyl, $C_{6-14}$-aryl, and a 5 to 14 membered heterocyclic ring system, and wherein wherein
$R^b$ is at each occurrence selected from the group consisting of $C_{1-20}$-alkyl, $C_{2-20}$-alkenyl, $C_{2-20}$-alkynyl, $C_{4-8}$-cycloalkyl, $C_{6-14}$-aryl, and a 5 to 14 membered heterocyclic ring system, wherein
$C_{1-20}$-alkyl, $C_{2-20}$-alkenyl or $C_{2-20}$-alkynyl may be substituted with 1 to 5 residues at each occurrence selected from the group consisting of halogen, CN, —NO$_2$, —OH, —NH$_2$, $C_{4-8}$-cycloalkyl, $C_{6-14}$-aryl, and a 5 to 14 membered heterocyclic ring system, and
$C_{6-14}$-aryl, and a 5 to 14 membered heterocyclic ring system may be substituted with 1 to 5 residues independently selected from the group consisting of halogen, CN, —NO$_2$, —OH, —NH$_2$, $C_{1-10}$-alkyl, $C_{2-10}$-alkenyl, and $C_{2-10}$-alkynyl.

Most preferred are compounds of formula

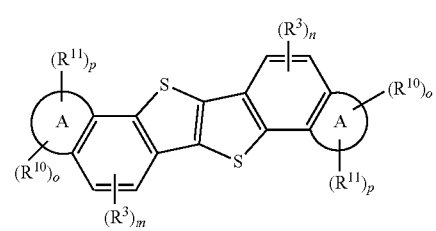

(1)

wherein
o is 1 or 2,
p is 0 or 1,
n is 0 or 1,
m is 0 or 1,
A is

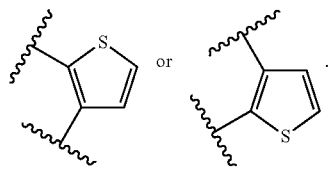 [SMILES: *c1ccsc1* ; *c1ccsc1*]

$R^{10}$ is at each occurrence $C_{8-20}$-alkyl, and
$R^3$ and $R^{11}$ are independently from each other at each occurrence $C_{1-30}$-alkyl.

In particular preferred compounds of formula (1) are the compounds of formulae

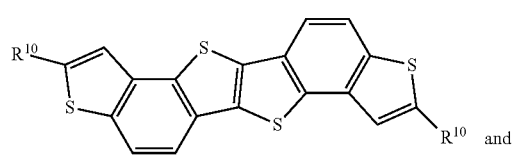
(1'a)

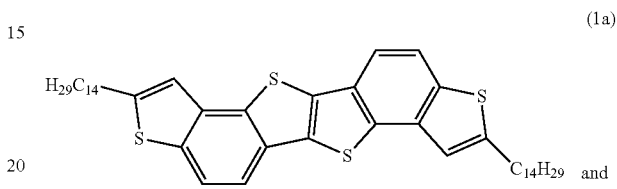
(1'b)

wherein $R^{10}$ is $C_{8-20}$-alkyl.

Even more particular preferred compounds of formula (1) are the compounds of formulae

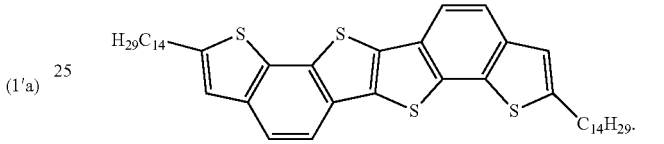
(1a) and (1b)

The compounds of formula (1) can be prepared by methods known in the art.

For example, the compound of formula (1a) can be prepared as outlined below:

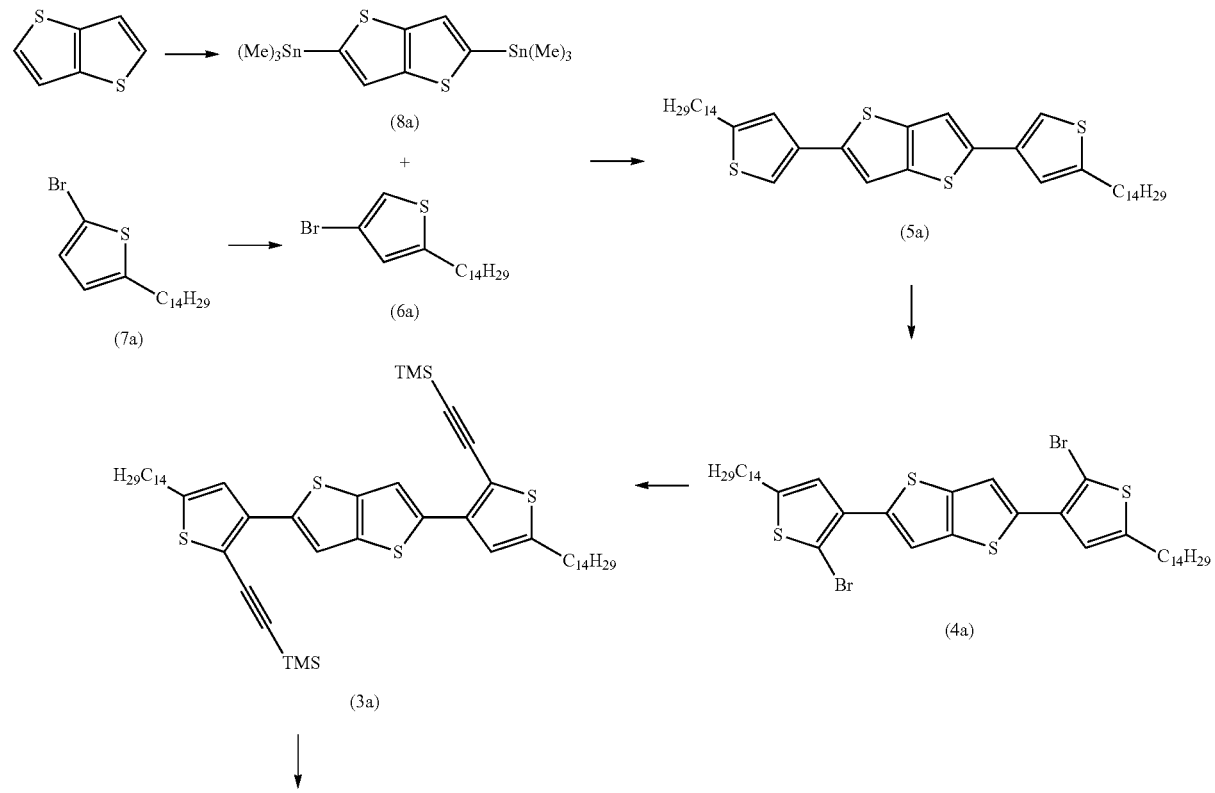

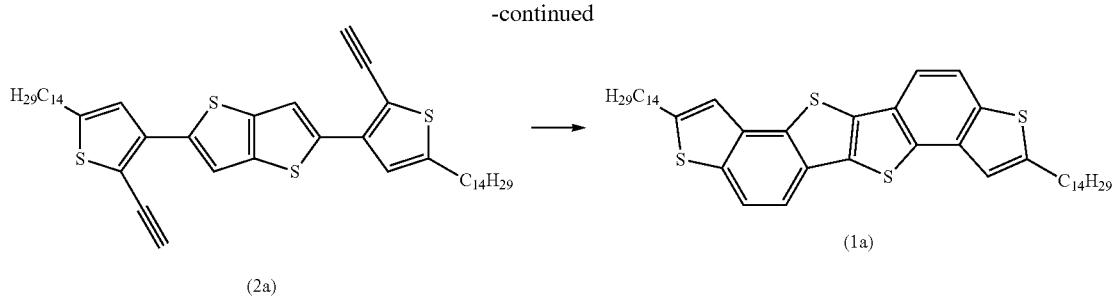

(2a)　　　　　　　　　　　　　　　(1a)

The compound of formula (1a) can be prepared by treating a compound of formula (2a) with a suitable catalyst such as PtCl$_2$, usually at elevated temperatures such as at between 50° C. and 120° C., and in the presence of an inert solvent such as toluene.

The compound of formula (2a) can be prepared by treating a compound of formula (3a) with K$_2$CO$_3$ in a suitable solvent such as methanol/tetrahydrofuran, usually at ambient temperatures such as between 18° C. and 30° C.

The compound of formula (3a) can be prepared by treating a compound of formula (4a) with trimethyl(2-tributylstannylethynyl)silane and a suitable catalyst such as Pd(PPh$_3$)$_4$, usually at elevated temperatures such as between 60° C. and 180° C., usually in the presence of a suitable solvent such as dimethylformamide.

The compound of formula (4a) can be prepared by treating compound of formula (5a) with a halogen-donating agent, especially a bromine-donating agent such as Br$_2$ or N-bromo-succinimide, usually at temperatures between −5° C. and 30° C., and usually in the presence of an inert solvent such as chloroform.

The compound of formula (5a) can be prepared by reacting a compound of formula (8a) with a compound of formula (6a) in the presence of a suitable solvent such as Pd(PPh$_3$)$_4$, usually at elevated temperatures such as between 50° C. and 180° C., and usually in the presence of a suitable solvent such as dimethylformamide.

The compound of formula (6a) can be prepared by adding a compound of formula (7a) to a solution of lithiumdimethylamide in tetrahydrofuran.

The compound of formula (8a) can be prepared by treating thieno[3,2-b]thiophene first with n-butyllithium at −78° C. in tetrahydrofuran, and then with trimethyltin chloride at −78° C. in tetrahydrofurane.

For example, the compound of formula (1b) can be prepared as outlined below:

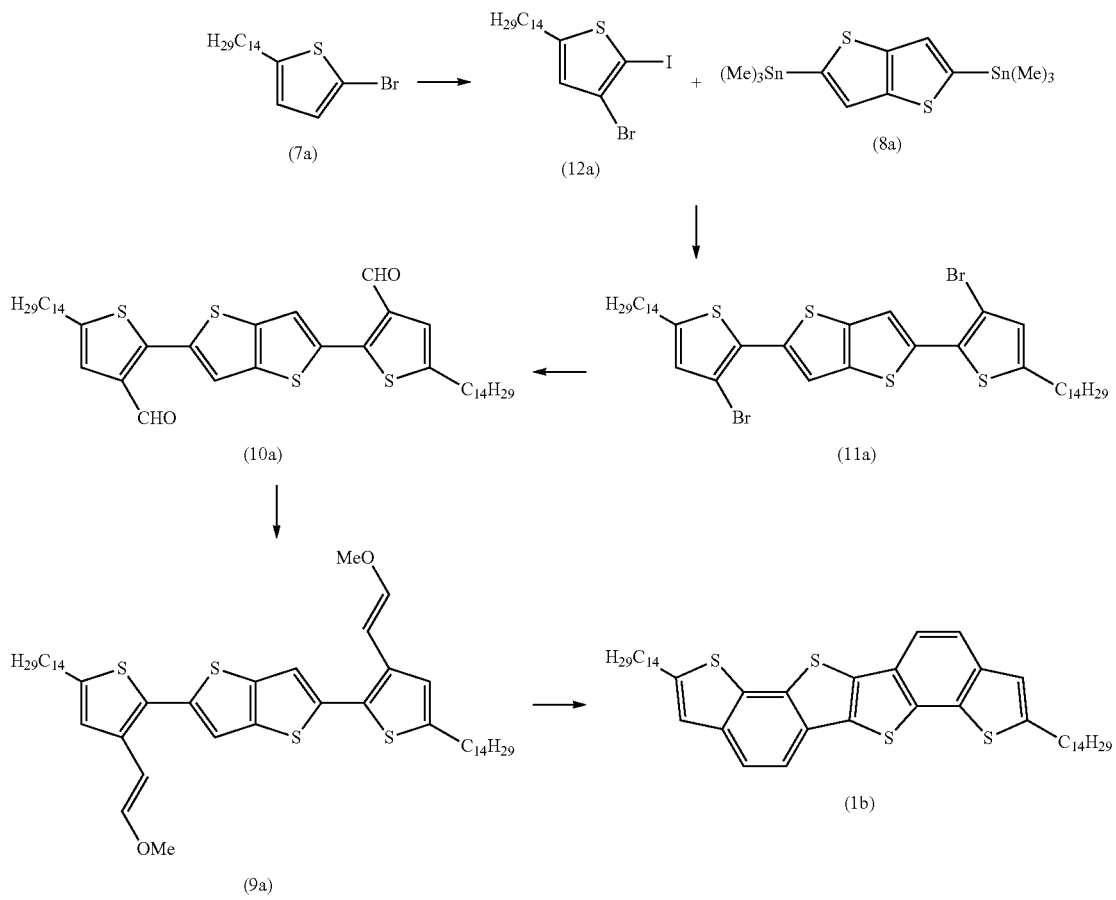

The compound of formula (1b) can be prepared by treating a compound of formula (9a) with methanesulfonic acid, usually in an inert solvent such dichloromethane, and usually at temperatures between −5° C. and 30° C.

The compound of formula (9a) can be prepared by adding a compound of formula (10a) to a solution obtained by treating a solution of (methoxymethyl)triphenylphosphonium chloride in tetrahydrofurane with potassium tert-butoxide. The reaction is usually performed at a temperature in the range of from −5° C. to 30° C.

The compound of formula (10a) can be prepared by treating a compound of formula (11a) first with butyllithium in tetrahydrofurane at −78° C., followed by treatment with dimethylformamide.

The compound of formula (11a) can be prepared by reacting a compound of formula (8a) with a compound of formula (12a) in the presence of a suitable catalyst such as $Pd(PPh_3)_4$, and in the presence of a suitable solvent such as dimethylformamide.

The compound of formula (12a) can be prepared by first adding a compound of formula (7a) to a solution of lithiumdimethylamide in tetrahydrofuran at −78° C., and then by adding the so-obtained solution to a solution of iodine in tetrahydrofurane at −78° C.

Also part of the present invention is an electronic device comprising the compound of formula (1). Preferably, the electronic device is an organic field effect transistor (OFET).

Usually, an organic field effect transistor comprises a dielectric layer, a semiconducting layer and a substrate. In addition, an organic field effect transistor usually comprises a gate electrode and source/drain electrodes.

Preferably, the compound of formula (1) is present in the semiconducting layer. The semiconducting layer can have a thickness of 5 to 500 nm, preferably of 10 to 100 nm, more preferably of 20 to 50 nm.

The dielectric layer comprises a dielectric material. The dielectric material can be silicon dioxide, or, an organic polymer such as polystyrene (PS), poly(methylmethacrylate) (PMMA), poly(4-vinylphenol) (PVP), poly(vinyl alcohol) (PVA), benzocyclobutene (BCB), or polyimide (PI). The dielectric layer can have a thickness of 10 to 2000 nm, preferably of 50 to 1000 nm, more preferably of 100 to 800 nm.

The source/drain electrodes can be made from any suitable source/drain material, for example gold (Au) or tantalum (Ta). The source/drain electrodes can have a thickness of 1 to 100 nm, preferably from 20 to 70 nm.

The gate electrode can be made from any suitable gate material such as highly doped silicon, aluminium (Al), tungsten (W), indium tin oxide, gold (Au) and/or tantalum (Ta). The gate electrode can have a thickness of 1 to 200 nm, preferably from 5 to 100 nm.

The substrate can be any suitable substrate such as glass, or a plastic substrate such as polyethersulfone, polycarbonate, polysulfone, polyethylene terephthalate (PET) and polyethylene naphthalate (PEN). Depending on the design of the organic field effect transistor, a combination of the gate electrode and the dielectric layer can also function as substrate.

The organic field effect transistor can be prepared by methods known in the art.

For example, a bottom-gate top-contact organic field effect transistor can be prepared as follows: The gate electrode can be formed by depositing the gate material, for example highly doped silicon, on one side of the dielectric layer made of a suitable dielectric material, for example silicium dioxide. The semiconducting layer can be formed by either solution deposition or thermal evaporation in vacuo of a compound of formula (1) on the other side of the dielectric layer. Source/drain electrodes can be formed by deposition of a suitable source/drain material, for example tantalum (Ta) and/or gold (Au), on the semiconducting layer through a shadow masks. The channel width (W) is typically 50 μm and the channel length (L) is typically 1000 μm.

Also part of the invention is the use of the compound of formula (1) as semiconducting material.

The compounds of formula (1) show a high charge carrier mobility and a high stability, in particular towards oxidation, under ambient conditions. Furthermore the compounds of formula (1) are compatible with liquid processing techniques.

BRIEF DESCRIPTION OF THE DRAWINGS

FIG. 1 shows the design of the bottom-gate, top-contact organic field effect transistor of example 3.

FIG. 2 shows the drain current $I_d$ [A] in relation to the gate-source voltage $V_g$ [V] (top transfer curve) and the drain current $I_d^{1/2}$ [$A^{1/2}$] in relation to the gate-source voltage $V_g$ [V] (bottom transfer curve) for the bottom-gate top-contact organic field effect transistor of example 3 comprising compound 1b as semiconducting material at a drain voltage $V_d$ of −60 V.

FIG. 3 shows the drain current $I_d$ [A] in relation to the drain voltage $V_d$ [V] (output curves) for the bottom-gate, top-contact organic field effect transistor of example 3 comprising compound 1b as semiconducting material at a gate-source voltage $V_g$ of −60 V (first and top curve), −40 V (second curve), −20 V (third curve) and 0 V (fourth and bottom curve).

FIG. 4 shows the drain current $I_d$ [A] in relation to the gate-source voltage $V_g$ [V] (top transfer curve) and the drain current $I_d^{1/2}$ [$10^{-3} A^{1/2}$] in relation to the gate-source voltage $V_g$ [V] (bottom transfer curve) for the bottom-gate top-contact organic field effect transistor of example 3 comprising compound 1a as semiconducting material at a drain voltage $V_d$ of −40 V.

FIG. 5 shows the drain current $I_d$ [A] in relation to the drain voltage $V_d$ [V] (output curves) for the bottom-gate, top-contact organic field effect transistor of example 3 comprising compound 1a as semiconducting material at a gate-source voltage $V_g$ of −60 V (first and top curve), −55 V (second curve), −50 V (third curve) and −45 V (fourth and bottom curve).

EXAMPLES

Example 1

Preparation of Compound 1a

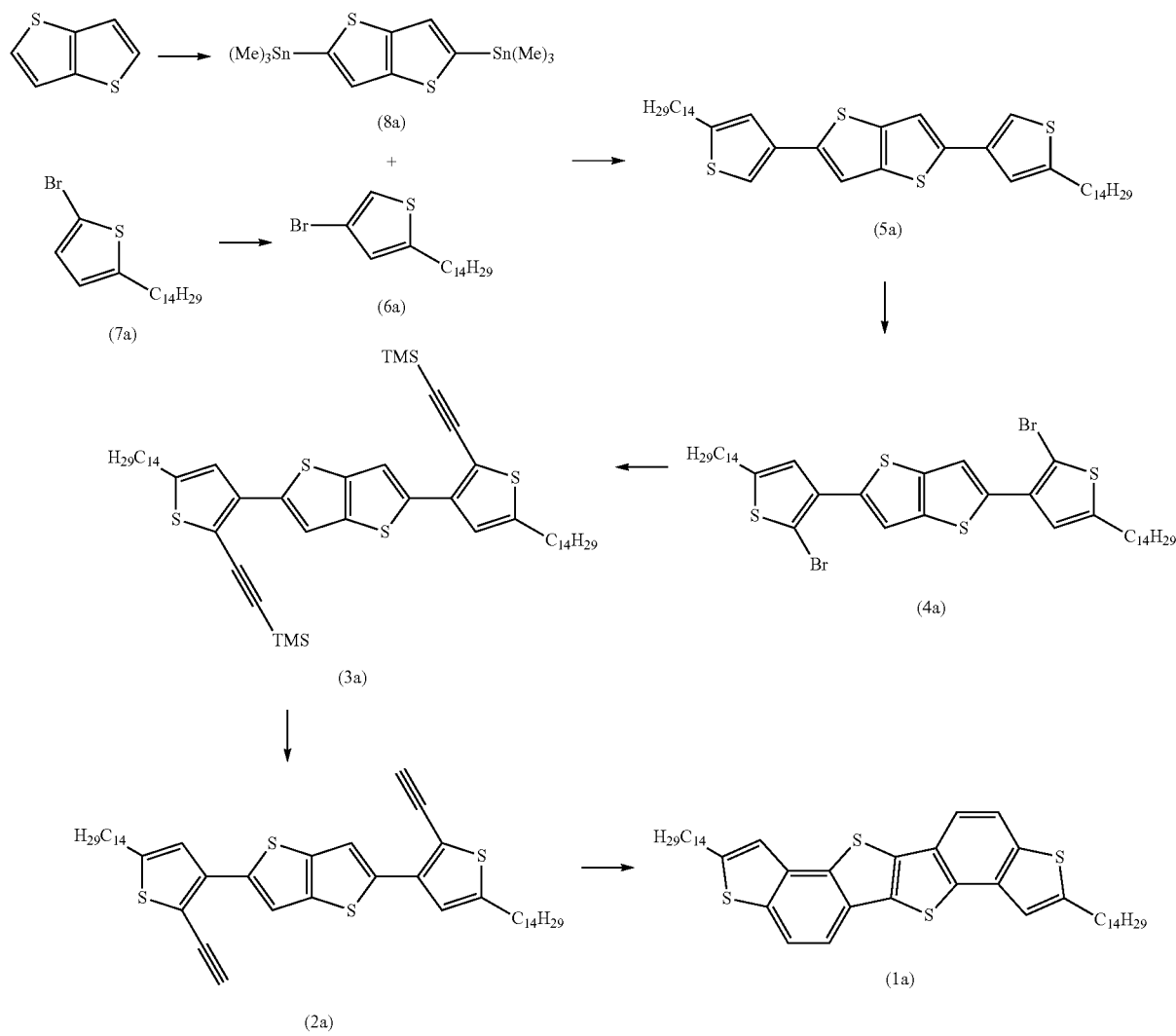

Preparation of Compound 8a

Commercially available thieno[3,2-b]thiophene (4 g, 32 mmol) in THF (100 mL) was cooled to −78° C. and n-butyllithium solution (1.6 M, 42 mL, 66 mmol) was added drop wise over 60 minutes using a dropping funnel. The reaction mixture was gradually warmed to room temperature and stirred for 3 hrs. The resultant suspension was again cooled to −78° C. and a solution of trimethyltin chloride (13.15 g, 66 mmol) in THF (50 mL) was added drop wise over 30 minutes using a dropping funnel. The resultant mixture was gradually warmed to room temperature and stirred for 16 hrs. The reaction mixture was quenched with water (150 mL) and extracted with $Et_2O$ (2×100 mL). Combined organic layers were washed with brine and concentrated to give brown solids, which were triturated with ethanol (4×20 mL). The solids were collected by filtration and washed thoroughly with ethanol (2×20 mL) to yield compound 8a as a white solid (10 g, 68%), which was used directly in the next step without further purification.

$^1$H NMR (400 MHz, $CDCl_3$) δ 7.26 (s, 2H), 0.37 (s, 18H).

Preparation of Compound 6a

Commercially available LDA solution (2 M, 24 mL, 47 mmol) was diluted in THF (65 mL) solution at 0° C. A solution of 2-bromo-5-tetradodecyl-thiophene (7a) (14 g, 39 mmol) in THF (65 mL) was added drop wise to the dilute LDA solution at 0° C. over 1 h using a dropping funnel. The resultant mixture was gradually warmed to room temperature and stirred for 3 hrs. The reaction mixture was quenched with water (150 mL) and extracted with $Et_2O$ (2×100 mL). The combined organic layers were washed with brine and concentrated to give a brown oil, which was purified by column chromatography on silica gel using 100% hexane to yield compound 6a as yellow oil (12.5 g, 89%). $^1$H NMR (400 MHz, $CDCl_3$) δ 6.99 (s, 1H), 6.70 (s, 1H), 2.77 (t, 2H, J=8 Hz), 1.65 (q, 2H, J=8 Hz), 1.44-1.20 (m, 22H), 0.89 (t, 3H, J=6.8 Hz).

Preparation of Compound 5a

A solution of compound 8a (6.35 g, 13.6 mmol), compound 6a (10.75 g, 30 mmol) and $Pd(PPh_3)_4$ (1.58 g, 1.36 mmol) were mixed in DMF (60 mL) and stirred at 90° C. for 4 hrs. The resultant suspension was diluted with $H_2O$ (100 mL) and the solids were isolated by filtration. The solids were taken up in a hexane/ethyl acetate mixture (v/v 3:1, 60 mL) and the slurry was stirred for 30 minutes at 60° C. The resultant suspension was cooled to room temperature and the solids were collected by filtration, and washed thoroughly with hexane (3×20 mL) to yield compound 5a as yellow solid (6.6 g, 69%). $^1$H NMR (400 MHz, CDCl$_3$) δ 7.26 (s, 2H), 6.99 (s, 2H), 6.70 (s, 2H), 2.81 (t, 4H, J=7.6 Hz), 1.70 (m, 4H, J=7.6 Hz), 1.44-1.20 (m, 44H), 0.87 (t, 6H, J=7.6 Hz).

Preparation of Compound 4a

A solution of compound 5a (6.6 g, 9.46 mmol) in CHCl$_3$ (200 mL) was treated with N-bromo-succinimide (3.7 g, 20.8 mmol) portion wise over 30 minutes at 0° C. The resultant mixture was gradually warmed to room temperature and stirred for 3 hrs. H$_2$O (300 mL) was added to the reaction mixture and extracted with CH$_2$Cl$_2$ (3×60 mL). The combined organic layers were dried and concentrated to give a brown solid. The solid was taken up in a hexane/ethyl acetate mixture (v/v 3:1, 100 mL) and stirred for 30 minutes at 60° C. The resultant solids were collected by filtration and washed thoroughly with hexane (3×10 mL) to yield compound 4a as yellow solid (6.3 g, 77%). $^1$H NMR (400 MHz, CDCl$_3$) δ 7.60 (s, 2H), 6.83 (s, 2H), 2.74 (t, 4H, J=7.6 Hz), 1.67 (m, 4H, J=7.6 Hz), 1.44-1.20 (m, 44H), 0.87 (t, 6H, J=6.8 Hz).

Preparation of Compound 3a

Compound 4a (2.56 g, 3 mmol), trimethyl(2-tributylstannylethynyl)silane (3.50 g, 9 mmol) and Pd(PPh$_3$)$_4$ (350 mg, 0.3 mmol) were mixed in DMF (50 mL) and stirred at 120° C. for 3 hrs. The reaction mixture was diluted with H$_2$O (150 mL) and extracted with CH$_2$Cl$_2$ (3×60 mL). The combined organic layers were dried and concentrated in vacuo to give a brown oil, which was purified by column chromatography on silica gel using 100% hexane to give compound 3a as yellow solid (2 g, 74%). $^1$H NMR (400 MHz, CDCl$_3$) δ 7.81 (s, 2H), 6.90 (s, 2H), 2.76 (t, 4H, J=7.6 Hz), 1.63 (m, 4H, J=7.6 Hz), 1.44-1.20 (m, 44H), 0.92 (t, 6H, J=7.2 Hz), 0.30 (s, 18H).

Preparation of Compound 2a

A reaction mixture of compound 3a (1.90 g, 2.15 mmol) and K$_2$CO$_3$ (1.13 g, 8.15 mmol) in MeOH/THF (v/v 1:1, 60 mL) mixture was stirred at room temperature for 20 hrs. The resultant suspension was diluted with THF (20 mL) and filtered. The residue was washed thoroughly with CH$_2$Cl$_2$ (20 mL) and the filtrate was concentrated in vacuo. The resultant crude solids were purified by column chromatography on silica gel using 100% hexane to yield compound 2a as yellow solid (0.8 g, 50%). $^1$H NMR (400 MHz, CDCl$_3$) δ 7.81 (s, 2H), 6.90 (s, 2H), 3.68 (s, 2H), 2.77 (t, 4H, J=7.6 Hz), 1.68 (m, 4H), 1.44-1.20 (m, 44H), 0.87 (t, 6H, J=7.2 Hz).

Preparation of Compound 1a

Compound 2a (100 mg, 0.134 mmol) and PtCl$_2$ (16 mg, 0.027 mmol) were mixed in toluene (20 mL) and heated at 60° C. for 20 hrs. The reaction mixture was cooled to room temperature and filtered. The filtrate was concentrated and purified by column chromatography on silica gel using hexane/toluene (v/v 3:1) to yield compound 1a as yellow solid (8 mg, 8%). $^1$H NMR (400 MHz, CDCl$_3$) δ 7.81 (d, 2H, J=8.4 Hz), 7.76 (d, 2H, J=8.4 Hz), 2.99 (t, 4H, J=7.6 Hz), 1.81 (m, 4H, J=7.6 Hz), 1.45-1.15 (m, 44H), 0.87 (t, 6H, J=6.8 Hz).

Example 2

Preparation of Compound 1 b

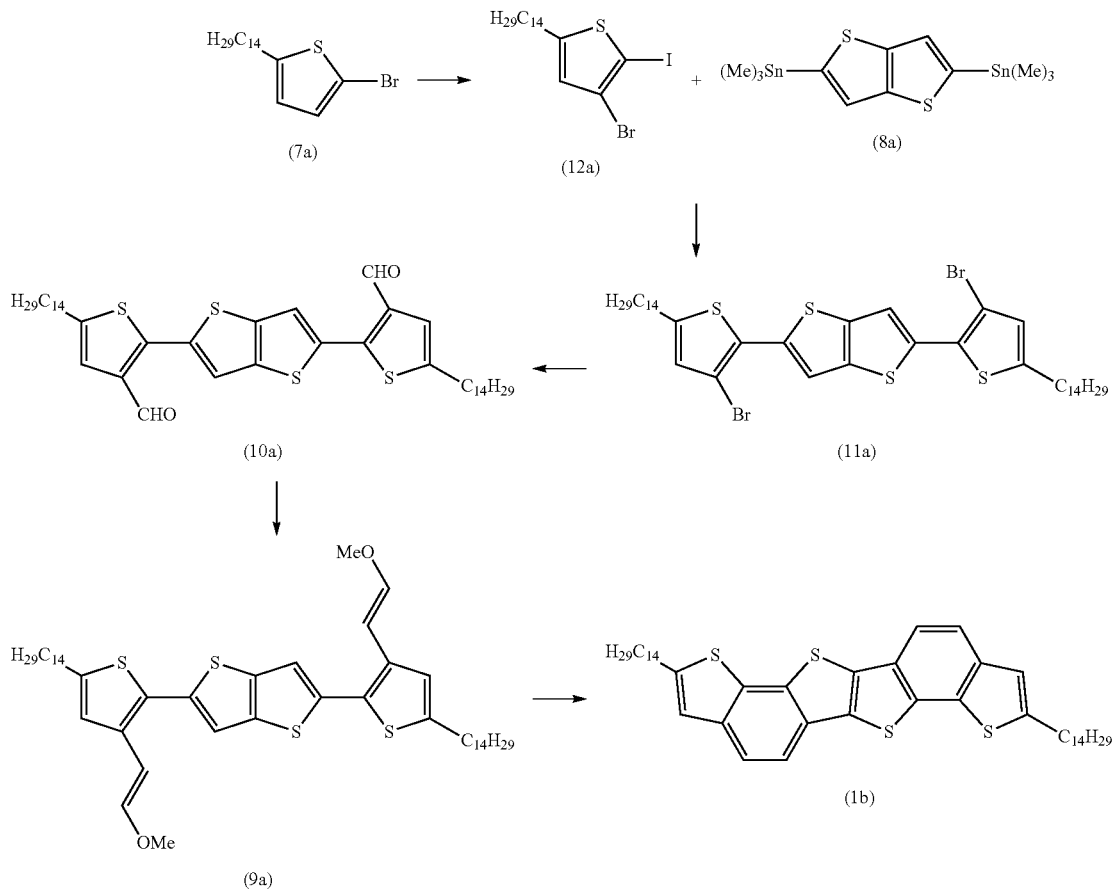

Preparation of Compound 12a

Commercially available LDA solution (2 M, 10 mL, 20.0 mmol) was diluted in THF (75 mL) solution at 0° C. A solution of compound 7a (6 g, 16.7 mmol) in THF (75 mL) was added drop wise to the dilute LDA solution at 0° C. using a dropping funnel. The resultant mixture was gradually warmed to room temperature and stirred for 3 hrs. The reaction mixture was then cooled to −78° C. and transferred via cannula into a cooled solution of $I_2$ in THF (150 mL) at −78° C. The reaction mixture was allowed to stir at this temperature for 2 hrs. The reaction mixture was quenched with water (150 mL) and extracted with $Et_2O$ (2×150 mL). The combined organic layers were washed with $Na_2S_2O_3$, dried over $MgSO_4$ and concentrated. The crude material was purified by column chromatography on silica gel using 100% hexane to yield compound 12a as yellow oil (7 g, 86%). $^1$H NMR (400 MHz, $CDCl_3$) δ 6.60 (s, 1H), 2.75 (t, 2H, J=7.2 Hz), 1.62 (m, 2H, J=7.2 Hz), 1.30-1.25 (m, 22H), 0.89 (t, 3H, J=7.2 Hz).

Preparation of Compound 11a

Compound 8a, prepared as described in example 1, (2.3 g, 4.93 mmol), compound 12a (6.7 g, 13.8 mmol) and $Pd(PPh_3)_4$ (0.6 g, 0.49 mmol) were added in a reaction vessel and evacuated 3 times with nitrogen. DMF (49 mL) was then added and stirred at 70° C. for 22 h. The resultant suspension was diluted with $H_2O$ (100 mL) and the solids were isolated by filtration. The solids were washed thoroughly with $H_2O$ (5×50 mL) and hexane (20 mL) to yield compound 11a as orange solid (4 g, 95%). $^1$H NMR (400 MHz, $CDCl_3$) δ 7.52 (s, 2H), 6.73 (s, 2H), 2.76 (t, 4H, J=7.6 Hz), 1.67 (m, 4H, J=7.6 Hz), 1.36-1.26 (m, 44H), 0.88 (t, 6H, J=7.6 Hz).

Preparation of Compound 10a

Into a solution of compound 11a in 8 mL anhydrous THF at −78° C., 1.6 M n-BuLi (0.55 mL, 0.88 mmol) was added dropwise within 15 minutes. The solution changed from greenish yellow to slurry orange solution. After 2 hrs stirring at −78° C., DMF (0.1 mL, 1.2 mmol) in 2 mL anhydrous THF was added. The reaction mixture was slowly allowed to warm up to room temperature and stirred overnight. The mixture was poured into 30 mL water and then extracted with diethyl ether (3×20 mL). The organic layer was washed with water (3×20 mL), dried over anhydrous $MgSO_4$, and concentrated. The orange solid was purified by column chromatography using hexane/toluene (v/v 3:1) to give compound 10a as orange crystalline solid (202 mg, 67%).

$^1$H NMR (400 MHz, $CD_2Cl_2$) δ 10.08 (s, 2H), 7.48 (s, 2H), 7.22 (s, 2H), 2.82 (t, 4H, J=8 Hz), 1.71 (m, 4H, J=7.6 Hz), 1.40-1.27 (m, 44H), 0.88 (t, 6H, J=6.8 Hz).

Preparation of Compound 9a

Into a slurry white solution of (methoxymethyl) triphenylphosphonium chloride (1.061 g, 3.1 mmol) and 20 mL anhydrous THF at 0° C., cooled on ice bath, anhydrous potassium tert-butoxide (321 mg, 2.86 mmol) was added, the reaction turned into orange solution immediately and followed by stirring for 1 h at 0° C. The compound 10a (377 mg, 0.5 mmol) was added, the reaction solution was warmed up to room temperature and stirred for 3 hrs. The mixture was washed with water (20 mL), extracted with toluene (3×20 mL). The organic layer was collected, washed with water, dried with anhydrous $MgSO_4$, and concentrated. The orange residue was purified by column chromatography using hexane/toluene (v/v 9:1) to give compound 9a as orange solid (307 mg, 76%). $^1$H NMR (400 MHz, $CD_2Cl_2$) δ 7.21 (s, 2H), 7.03 (d, 2H, J=13.2 Hz), 6.77 (s, 2H), 6.10 (d, 2H, J=13.2 Hz), 3.68 (s, 6H), 2.76 (t, 4H, J=8 Hz), 1.68 (m, 4H, J=7.6 Hz), 1.39-1.27 (m, 44H), 0.88 (t, 6H, J=7.2 Hz).

Preparation of Compound 1b

Into a 50 mL Schlenk flask covered with aluminium foil, compound 9a (81 mg, 0.1 mmol) was dissolved in 2 mL of anhydrous dichloromethane. The solution was cooled on ice. After the addition of 1 drop of methanesulfonic acid, the reaction solution was warmed up to room temperature and stirred overnight. The precipitates were filtered and washed with methanol to yield a yellow solid. The crude compound 1b was recrystallized from hot hexane to yield compound 1b as yellow solid (45 mg, 60%). $^1$H NMR (400 MHz, $CD_2Cl_2$) δ 7.80 (d, 2H, J=8.4Hz), 7.74 (d, 2H, J=8.4Hz), 7.16 (s, 2H), 2.98 (t, 4H, J=7.6 Hz), 1.80 (q, 4H, J=7.6 Hz), 1.45-1.21(m, 44H), 0.87 (t, 6H, J=7.2 Hz).

Example 3

Preparation of Bottom-Gate, Top-Contact Organic Field Effect Transistors (OFETs) Comprising Compound 1a, Respectively, 1b as Semiconducting Material Thermally grown silicon dioxide (thickness: 200 nm) was used as dielectric layer. The gate electrode was formed by depositing highly doped silicon on one side of the dielectric layer. The semiconducting layer was formed by evaporation of compound 1a, respectively, by either evaporation or solution deposition (chlorobenzene, 1 mg/ml, drop casting at 70° C.) of compound 1b on the other side of the dielectric layer. Source/drain Au electrodes (thickness: 50 nm) were deposited through a shadow mask to give top-contact OFET devices. The channel width (W) was typically 50 μm and channel length (L) is 1000 μm.

The design of the bottom-gate, top-contact organic field effect transistor of example 3 is shown in FIG. 1.

Example 4

Measurement of the Transfer Curves and the Output Curves of the Bottom-Gate, Top-Contact Organic Field Effect Transistors (OFETs) Comprising Compound 1a, Respectively, 1b The drain current $I_d$ [A] in relation to the gate-source voltage $V_g$ [V] (top transfer curve) and the drain current $I_d^{1/2}$ [$A^{1/2}$] in relation to the gate-source voltage $V_g$ [V] (bottom transfer curve) for the bottom-gate top-contact organic field effect transistor of example 3 comprising compound 1b as semiconducting material at a drain voltage $V_d$ of −60 V was determined in air at room temperature using a Keithley 4200 machine. The results are shown in FIG. 2.

The drain current $I_d$ [A] in relation to the drain voltage $V_d$ [V] (output curves) for the bottom-gate, top-contact organic field effect transistor of example 3 comprising compound 1b as semiconducting material at a gate-source voltage $V_g$ of −60 V (first and top curve), −40 V (second curve), −20 V (third curve) and 0 V (fourth and bottom curve) was determined in air at ambient temperature using a Keithley 4200 machine. The results are shown in FIG. 3.

The drain current $I_d$ [A] in relation to the gate-source voltage $V_g$ [V] (top transfer curve) and the drain current $I_d^{1/2}$ [$10^{-3} A^{1/2}$] in relation to the gate-source voltage $V_g$ [V] (bottom transfer curve) for the bottom-gate top-contact organic field effect transistor of example 3 comprising compound 1a as semiconducting material at a drain voltage $V_d$ of −40 V was determined in air at room temperature using a Keithley 4200 machine. The results are shown in FIG. 4.

The drain current $I_d$ [μA] in relation to the drain voltage $V_d$ [V] (output curves) for the bottom-gate, top-contact organic field effect transistor of example 3 comprising compound 1a as semiconducting material at a gate-source voltage $V_g$ of −60 V (first and top curve), −55 V (second curve), −50 V (third curve) and −45 V (fourth and bottom curve) was determined in air at ambient temperature using a Keithley 4200 machine. The results are shown in FIG. 5.

The compounds 1a and 1b show the typical behavior of a p-type semiconducting material.

The charge-carrier mobility was extracted in the saturation regime from the slope of $I_d^{1/2}$ [$μA^{1/2}$] versus $V_g$ [V]. The threshold voltage $V_{th}$ [V] was obtained using the following equation:

$$\mu = 2I_d / \{(W/L)C_\mu(V_g - V_{th})^2\}$$

wherein $C\mu$ is the capacitance of the dielectric layer.

The average values of the charge carrier mobility $\mu_{sat}$ [cm$^2$/V s], the $I_{ON}/I_{OFF}$ ratio and the threshold voltage $V_{th}$ [V] for the bottom-gate, top-contact organic field effect transistor of example 3 comprising compound 1a, respectively, 1b as semiconducting material are given in table 1.

TABLE 1

| Compounds | process of deposition of semiconducting layer | $\mu_{sat}$ [cm$^2$/V s] | $I_{on}/I_{off}$ | $V_{th}$ [V] |
|---|---|---|---|---|
| 1a | Evaporation | 0.90 | 3 * 10$^8$ | −47 |
| 1b | Solution | 8 * 10$^{-3}$ | 5 * 10$^3$ | −39 |
| 1b | Evaporation | 0.03 | 1 * 10$^5$ | −47 |

Example 5

Preparation of Compound 1a

Preparation of Compound 12a

A solution of 5a (7.8 g, 11.2 mmol), prepared as described in example 1, in CH$_2$Cl$_2$ (100 ml) was added drop wise to a mixture of POCl$_3$ and DMF in CH$_2$Cl$_2$ over 30 minutes at 0° C. The resultant mixture was gradually warmed to room temperature and stirred in a 40° C. hot water bath for 2 hours. The reaction mixture was diluted with CH$_2$Cl$_2$ and poured into ice (250 g) and stirred. KOAc (25 g) was added portion wise into the cold solution and mixed thoroughly. The organic layer was separated and concentrated to give crude product. The resultant solids were collected by filtration and washed thoroughly with CH$_2$Cl$_2$ (3×20 mL) to yield yellow solid (9.0 g, 98%).

$^1$H NMR (400 MHz, CDCl$_3$) δ 7.60 (s, 2H), 6.83 (s, 2H), 2.74 (t, 4H, J=7.6 Hz), 1.67 (q, 4H, J=7.6 Hz), 1.44-1.20 (m, 44H), 0.87 (t, 6H, J=6.8 Hz).

Preparation of Compound 13a 12a (2.4 g, 3.0 mmol) in THF (90 mL) was added drop wise to a mixture of (methoxymethyl)triphenylphosphonium chloride (6.2 g, 18 mmol) and KO$^t$Bu (2.0 g, 18 mmol) in THF (60 ml) at −50° C. in a dry ice-acetonitrile bath. The resultant mixture was left to stir in the cooling bath and slowly warmed to room temperature over 16 hrs. The reaction mixture was diluted with diethyl ether (100 mL) and brine (100 mL). The organic layer was separated and the aqueous layer further extracted with CH$_2$Cl$_2$ (3×50 mL). Combined organic layers were concentrated and purified by column chromatography on silica gel using hexanes/toluene (v/v 1:1) to give yellow solid (1.1 g, 42%). $^1$H NMR (400 MHz, CDCl$_3$) δ 7.21 (s, 2H), 6.96 (d, 2H, J=12.8 Hz), 6.79 (s, 2H), 6.24 (d, 2H, J=12.8 Hz), 3.69 (s, 2H), 2.77-2.70 (m, 4H), 1.62-1.75 (m, 4H), 1.45-1.20 (m, 44H), 0.87 (t, 6H, J=6.8 Hz).

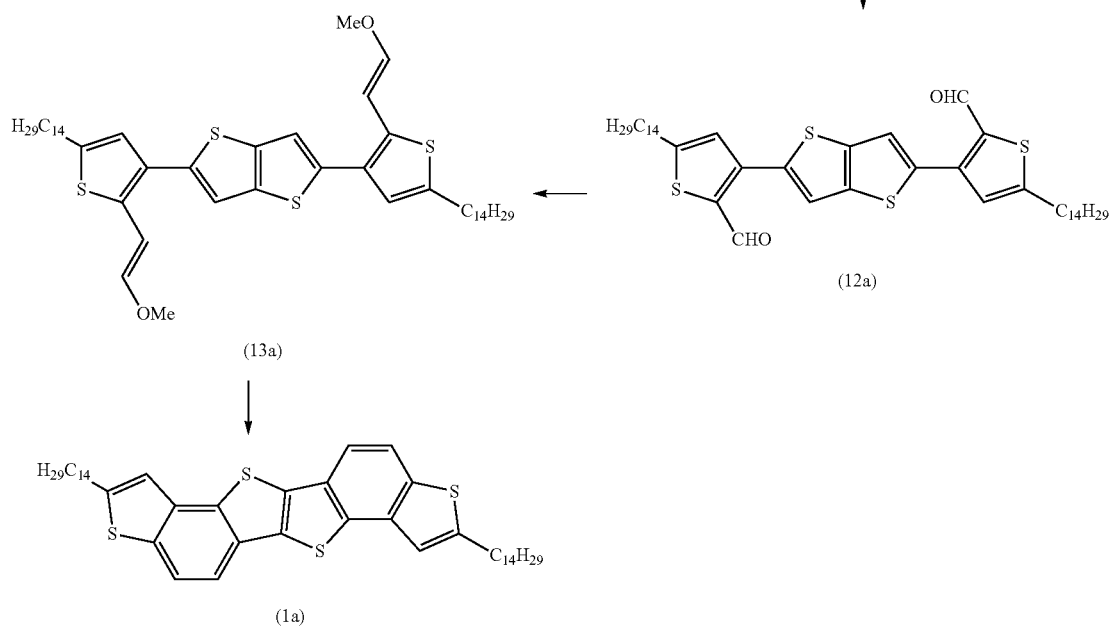

Preparation of Compound 1a

An isomeric mixture of 13a in $CH_2Cl_2$ (45 mL) was treated with methanesulfonic acid (0.05 mL) drop wise at 0° C. in the dark. The resultant mixture and stirred for 16 hrs at room temperature. The reaction mixture was concentrated to dryness and the resultant precipitate triturated with methylene chloride, then separated by filtration. The residue was washed with $H_2O$ and methanol. The crude product was recrystallized from hot hexanes to give yellow solid (0.5 g, 52%).

$^1H$ NMR (400 MHz, $CD_2Cl_2$) δ 7.84 (d, 2H, J=8.4 Hz), 7.77 (d, 2H, J=8.4 Hz), 7.27 (s, 2H), 2.98 (t, 4H, J=7.6 Hz), 1.75-1.85 (m, 4H), 1.40-1.20 (m, 44H), 0.85 (t, 6H, J=6.8 Hz).

The invention claimed is:
1. A compound of formula (1)

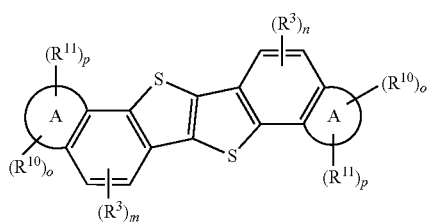

wherein
o is 1, 2 or 3,
p is 0, 1 or 2,
n is 0, 1 or 2,
m is 0, 1 or 2,
A is a mono -or dicyclic ring system A, which contains at least S atom,
wherein $R^{10}$ is at each occurrence $C_{1-30}$-alkyl, wherein
at least one $CH_2$-group of $C_{1-30}$-alkyl, but not adjacent $CH_2$-groups, is optionally replaced with —O— or —S—,
$C_{1-30}$-alkyl is optionally substituted with 1 to 10 $R^{100}$ residues at each occurrence selected from the group consisting of halogen, —CN, —$NO_2$, —OH, —$NH_2$, —NH($R^a$), —N($R^a$)$_2$, —NH—C(O)—($R^a$), —N($R^a$)—C(O)—($R^a$), —N[C(O)—($R^a$)]$_2$, —C(O)—$R^a$, —C(O)—$OR^a$, —C(O)$NH_2$, —CO(O)NH—$R^a$, —C(O)N($R^a$)$_2$, —O—$R^a$, —O—C(O)—$R^a$, $C_{4-8}$-cycloalkyl, $C_{6-14}$-aryl, and a 5 to 14 membered heterocyclic ring system, and
wherein
$R^a$ is at each occurrence selected from the group consisting of $C_{1-20}$-alkyl, $C_{2-20}$-alkenyl, $C_{2-20}$-alkynyl, $C_{4-8}$-cycloalkyl, $C_{6-14}$-aryl, and a 5 to 14 membered heterocyclic ring system, wherein
$C_{1-20}$-alkyl, $C_{2-20}$-alkenyl and $C_{2-20}$-alkynyl are optionally substituted with 1 to 5 residues at each occurrence selected from the group consisting of halogen, CN, —$NO_2$, —OH, —$NH_2$, $C_{4-8}$-cycloalkyl, $C_{6-14}$-aryl, and a 5 to 14 membered heterocyclic ring system;
$R^3$ and $R^{11}$ are independently from each other at each occurrence selected from the group consisting of halogen, —CN, —$NO_2$, $C_{1-30}$-alkenyl, $C_{2-30}$-alkenyl, $C_{2-30}$-alkynyl, $C_{4-8}$-cycloalkyl, $C_{6-14}$-aryl, and a 5 to 14 membered heterocyclic ring system, wherein at least one $CH_2$-group of $CH_{1-30}$-alkyl, $C_{2-30}$-alkenyl and $C_{2-30}$-alkynyl, but not adjacent $CH_2$-groups, is optionally replaced with —O— or —S—, and
$C_{1-30}$-alkyl, $C_{2-30}$-alkenyl and $C_{2-30}$-alkynyl are optionally substituted with 1 to 10 $R^{101}$ residues independently selected from the group consisting of halogen, —CN, —$NO_2$, —OH, —$NH_2$, —NH($R^b$), —N($R^b$)$_2$, —NH—C(O)—($R^b$), —N($R^b$)—C(O)—($R^b$), —N[C(O)—($R^b$)]$_2$, —C(O)—$R^b$, —C(O)—$OR^b$, —C(O)$NH_2$, —CO(O)NH—$R^b$, —C(O)N($R^b$)$_2$, —O—$R^b$, —O—C(O)—$R^b$, $C_{4-8}$-cycloalkyl, $C_{6-14}$-aryl, and a 5 to 14 membered heterocyclic ring system, and
wherein
$R^b$ is at each occurrence selected from the group consisting of $C_{1-20}$-alkyl, $C_{2-20}$-alkenyl, $C_{2-20}$-alkynyl, $C_{4-8}$-cycloalkyl, $C_{6-14}$-aryl, and a 5 to 14 membered heterocyclic ring system, wherein
$C_{1-20}$-alkyl, $C_{2-20}$-alkenyl or $C_{2-20}$-alkynyl are optionally substituted with 1 to 5 residues at each occurrence selected from the group consisting of halogen, CN, —$NO_2$, —OH, —$NH_2$, $C_{4-8}$-cycloalkyl, $C_{6-14}$-aryl, and a 5 to 14 membered heterocyclic ring system, and
$C_{4-8}$-cycloalkyl, $C_{6-14}$-aryl, and a 5 to 14 membered heterocyclic ring system are optionally substituted with 1 to 5 residues independently selected from the group consisting of halogen, CN, —$NO_2$, —OH, —$NH_2$, $C_{1-10}$-alkyl, $C_{2-10}$-alkenyl, and $C_{2-10}$-alkynyl.

2. The compound of claim 1, wherein A is

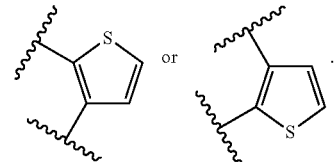 [SMILES: *c1ccsc1* ; *c1ccsc1*]

3. The compound of claim 1, wherein $R^{10}$ is at each occurrence $C_{8-20}$-alkyl.

4. The compound of claim 1, wherein $R^3$ and $R^{11}$ are independently from each other at each occurrence selected from the group consisting of halogen, —CN, $C_{1-30}$-alkyl, $C_{4-8}$-cycloalkyl, $C_{6-14}$-aryl, and a 5 to 14 membered heterocyclic ring system, wherein
at least one $CH_2$-group of $C_{1-30}$-alkyl, but not adjacent $CH_2$-groups, is optionally replaced with —O— or —S—, and
$C_{1-30}$-alkyl is optionally substituted with 1 to 10 $R^{101}$ residues independently selected from the group consisting of halogen, —CN, —$NO_2$, —OH, —$NH_2$, —NH($R^b$), —N($R^b$)$_2$, —NH—C(O)—($R^b$), —N($R^b$)—C(O)—($R^b$), —N[C(O)—($R^b$)]$_2$, —C(O)—$R^b$, —C(O)—$OR^b$, —C(O)$NH_2$, —CO(O)NH—$R^b$, —C(O)N($R^b$)$_2$, —O—$R^b$, —O—C(O)—$R^b$, $C_{4-8}$-cycloalkyl, $C_{6-14}$-aryl, and a 5 to 14 membered heterocyclic ring system, and wherein
wherein
$R^b$ is at each occurrence selected from the group consisting of $C_{1-20}$-alkyl, $C_{2-20}$-alkenyl, $C_{2-20}$-alkynyl, $C_{4-8}$-cycloalkyl, $C_{6-14}$-aryl, and a 5 to 14 membered heterocyclic ring system, wherein
$C_{1-20}$-alkyl, $C_{2-20}$-alkenyl or $C_{2-20}$-alkynyl is optionally substituted with 1 to 5 residues at each occurrence selected from the group consisting of halogen, CN, —$NO_2$, —OH, —$NH_2$, $C_{4-8}$-cycloalkyl, $C_{6-14}$-aryl, and a 5 to 14 membered heterocyclic ring system, and $C_{4-8}$-cycloalkyl, $C_{6-14}$-aryl, and a 5 to 14 membered heterocyclic ring system are optionally substituted with 1 to 5 residues independently selected from the group consisting of halogen, CN, —$NO_2$, —OH, —$NH_2$, $C_{1-10}$-alkyl, $C_{2-10}$-alkenyl, and $C_{2-10}$-alkynyl.

5. The compound of claim 1, wherein $R^3$ and $R^{11}$ are independently from each other at each occurrence selected from the group consisting of $C_{1-30}$-alkyl, $C_{6-14}$-aryl, and a 5 to 14 membered heterocyclic ring system, wherein at least one $CH_2$-group of $C_{1-30}$-alkyl, but not adjacent $CH_2$-groups, is optionally replaced with —O— or —S—, and $C_{1-30}$-alkyl is optionally substituted with 1 to 10 $R^{101}$ residues independently selected from the group consisting of halogen, —CN, —$NO_2$, —OH, —$NH_2$, —NH($R^b$), —N($R^b$)$_2$, —NH—C(O)—($R^b$), —N($R^b$)—C(O)—($R^b$), —N[C(O)—($R^b$)]$_2$, —C(O)—$R^b$, —C(O)—O$R^b$, —C(O)$NH_2$, —CO(O)NH—$R^b$, —C(O)N($R^b$)$_2$, —O—$R^b$, —O—C(O)—$R^b$, $C_{4-8}$-cycloalkyl, $C_{6-14}$-aryl, and a 5 to 14 membered heterocyclic ring system, and wherein wherein $R^b$ is at each occurrence selected from the group consisting of $C_{1-20}$-alkyl, $C_{2-20}$-alkenyl, $C_{2-20}$-alkynyl, $C_{4-8}$-cycloalkyl, $C_{6-14}$-aryl, and a 5 to 14 membered heterocyclic ring system, wherein $C_{1-20}$-alkyl, $C_{2-20}$-alkenyl or $C_{2-20}$-alkynyl is optionally substituted with 1 to 5 residues at each occurrence selected from the group consisting of halogen, CN, —$NO_2$, —OH, —$NH_2$, $C_{4-8}$-cycloalkyl, $C_{6-14}$-aryl, and a 5 to 14 membered heterocyclic ring system, and $C_{6-14}$-aryl, and a 5 to 14 membered heterocyclic ring system are optionally substituted with 1 to 5 residues independently selected from the group consisting of halogen, CN, —$NO_2$, —OH, —$NH_2$, $C_{1-10}$-alkyl, $C_{2-10}$-alkenyl, and $C_{2-10}$-alkynyl.

6. The compound of claim 1, wherein o is 1.

7. The compound of claim 1, wherein p, n and m are 0.

8. The compound of claim 1, wherein the compound of formula (1) is selected from the group consisting of formulae (1'a) and (1'b)

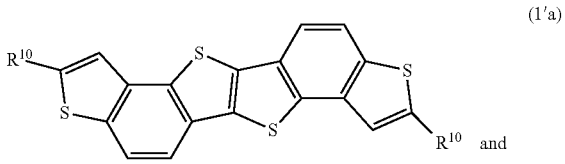

(1'a)

and

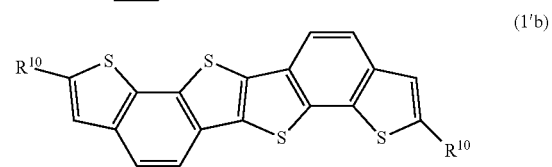

(1'b)

wherein $R^{10}$ is $C_{8-20}$-alkyl.

9. An electronic device comprising the compound according to claim 1.

10. The electronic device of claim 9, wherein the electronic device is an organic field effect transistor (OFET).

11. A method comprising incorporating the compound according to claim 1 as a semiconducting material.

* * * * *